US008265358B2

(12) United States Patent
Abe

(10) Patent No.: US 8,265,358 B2
(45) Date of Patent: Sep. 11, 2012

(54) ULTRASONIC IMAGE PROCESSING APPARATUS AND METHOD FOR PROCESSING ULTRASONIC IMAGE

(75) Inventor: Yasuhiko Abe, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 876 days.

(21) Appl. No.: 12/134,538

(22) Filed: Jun. 6, 2008

(65) Prior Publication Data

US 2008/0304730 A1    Dec. 11, 2008

(30) Foreign Application Priority Data

Jun. 6, 2007 (JP) ................................ 2007-149996

(51) Int. Cl.
*G06K 9/62* (2006.01)
*G06K 9/00* (2006.01)

(52) U.S. Cl. ........ 382/128; 382/131; 382/199; 600/437; 600/443; 600/463

(58) Field of Classification Search .......... 382/128–134; 600/407–464
See application file for complete search history.

(56) References Cited

U.S. PATENT DOCUMENTS

| | | | |
|---|---|---|---|
| 6,638,221 B2 | 10/2003 | Abe et al. | |
| 6,859,548 B2* | 2/2005 | Yoshioka et al. | 382/128 |
| 7,110,583 B2* | 9/2006 | Yamauchi | 382/128 |
| 7,460,698 B2* | 12/2008 | Yoshioka et al. | 382/128 |
| 7,507,204 B2* | 3/2009 | Shim et al. | 600/443 |
| 7,577,281 B2* | 8/2009 | Nishiura | 382/128 |
| 8,055,040 B2* | 11/2011 | Ohuchi et al. | 382/128 |
| 2003/0171668 A1* | 9/2003 | Tsujino et al. | 600/407 |
| 2005/0111717 A1* | 5/2005 | Yoshioka et al. | 382/128 |
| 2006/0033679 A1 | 2/2006 | Gunji | |
| 2009/0060306 A1* | 3/2009 | Ohuchi et al. | 382/128 |
| 2010/0195887 A1* | 8/2010 | Abe et al. | 382/131 |

FOREIGN PATENT DOCUMENTS

| | | |
|---|---|---|
| CN | 1442118 A | 9/2003 |
| CN | 1729937 A | 2/2006 |

(Continued)

OTHER PUBLICATIONS

U.S. Appl. No. 12/302,506, filed Nov. 26, 2008, Kawagishi et al.

(Continued)

*Primary Examiner* — Melissa Koval
*Assistant Examiner* — Emily Chan
(74) *Attorney, Agent, or Firm* — Oblon, Spivak, McClelland, Maier & Neustadt, L.L.P.

(57) ABSTRACT

A contour detector detects the contour of a specific tissue based on ultrasonic image data having been acquired in a predetermined time phase. A contour tracking part obtains the position of each of points composing the contour of a specific tissue in ultrasonic image data having been acquired in each time phase, by pattern matching for each time phase. A computing part obtains motion information indicating the motion state of a specific tissue in each time phase, based on the position of each of points composing the contour in each time phase. A display controller controls a display to display an ultrasonic image based on ultrasonic image data having been acquired in each time phase, for each time phase. Furthermore, the display controller controls the display to display the motion information in each time phase, on each occasion of each time phase.

24 Claims, 6 Drawing Sheets

FOREIGN PATENT DOCUMENTS

| | | |
|---|---|---|
| JP | 2002-306483 | 10/2002 |
| JP | 2003-175041 | 6/2003 |
| JP | 2003-250804 | 9/2003 |
| WO | WO 2007/138751 A1 | 12/2007 |

OTHER PUBLICATIONS

Office Action issued Mar. 21, 2012, in Japanese Patent Application No. 2007-149996.

* cited by examiner

ULTRASONIC IMAGE PROCESSING APPARATUS AND METHOD FOR PROCESSING ULTRASONIC IMAGE

BACKGROUND OF THE INVENTION

1. Field of the Invention

The present invention relates to: an ultrasonic image processing apparatus configured to obtain the motion state of a subject by using an ultrasonic image of the subject having been acquired with ultrasonic waves; and a method for processing an ultrasonic image.

2. Description of the Related Art

It is extremely important to objectively and quantitatively evaluate the functions of living body tissues such as the myocardium of a heart, for diagnoses of these living body tissues. For example, a quantitative evaluation method based on image data by acquiring image data of a heart using an ultrasonic imaging apparatus has been proposed.

For example, a method of obtaining motion information such as displacement and strain of a tissue by tracking the speckle pattern of images has been proposed (U.S. Pat. No. 6,638,221). This method, in which pattern matching is performed by using the speckle pattern of images, is referred to as Speckle Tracking (ST). From hereon, this method is sometimes referred to as the ST method.

For concrete example, in the case of evaluation of the function of the myocardium of a heart, ultrasonic waves are transmitted to the heart, whereby a plurality of tomographic image data acquired at different times are acquired. Then, by performing pattern matching of the endocardium of the heart by the ST method, it is possible to obtain wall motion information such as displacement and strain of the endocardium.

Further, a method of detecting the boundary between a tissue region and a blood region based on luminance information of an image and detecting the position of the boundary in real time has been proposed (Ultrasonic Imaging 5, 300-307(1983)). This method is referred to as the Acoustic Quantification (AQ) method. From hereon, this method is sometimes referred to as the AQ method.

However, in the abovementioned method of detecting the boundary in real time, only the contour of the tissue region is detected, but, for example, the movement of each point on the endocardium is not tracked. Therefore, vector information indicating the movement of each point on the endocardium cannot be obtained. As a result, it is impossible to analyze the wall motion of the myocardium.

On the other hand, by the abovementioned ST method, it is possible to acquire, for example, vector information indicating the movement of each point on the endocardium, and therefore, it is possible to analyze the wall motion of the myocardium. However, an operator needs to designate the boundary position of a region of interest (ROI) to be a tracking object, in a specific time phase. Therefore, it is difficult to analyze the motion of the region of interest in real time. For example, in a case where the contour of the endocardium is tracked, a tomographic image (a still image) acquired in a predetermined phase is displayed, and the operator needs to designate the boundary position of the endocardium while observing the tomographic image. Therefore, it is difficult to analyze the wall motion of the endocardium in real time.

Further, even the method stated in U.S. Pat. No. 6,638,221 has not been disclosed a concrete method for displaying motion information of a region of interest by the ST method.

As described above, in the conventional technique, it is difficult to analyze and display the motion of a region of interest in real time by using the vector information.

SUMMARY OF THE INVENTION

An object of the present information is to provide an ultrasonic image processing apparatus and an ultrasonic image processing method that can provide motion information of a specific tissue in real time.

A first mode of the present invention is an ultrasonic image processing apparatus comprising: a contour detector configured to receive ultrasonic image data acquired for each time phase by scanning a subject with ultrasonic waves, and detect a contour of a specific tissue based on the ultrasonic image data acquired in a predetermined time phase; a contour tracking part configured to obtain a position of each of points composing the detected contour in the ultrasonic image data acquired for the each time phase, by pattern matching for the each time phase; a computing part configured to obtain motion information indicating a motion state of the specific tissue in the each time phase, based on the position of each of the points composing the contour in the each time phase; and a display controller configured to control a display to display an ultrasonic image based on the ultrasonic image data acquired in the each time phase, for the each time phase, and moreover control the display to display the motion information in the each time phase obtained by the computing part, on each occasion of the each time phase.

According to the first mode, it becomes possible to obtain and display motion information of a tissue in each time phase in real time by detecting the contour of a specific tissue based on the ultrasonic image data acquired in a predetermined time phase and by obtaining the position of each of the points composing the detected contour through pattern matching for each time phase.

A second mode of the present invention is an ultrasonic image processing apparatus comprising: a contour tracking part configured to receive ultrasonic image data acquired for each time phase by scanning a subject with ultrasonic waves, and moreover receive designation of a contour of a specific tissue on an ultrasonic image based on the ultrasonic image data acquired in a predetermined time phase, thereby obtaining a position of each of points composing the designated contour in the ultrasonic image data acquired for the each time phase, by pattern matching for the each time phase; a computing part configured to obtain motion information indicating a motion state of the specific tissue in the each time phase, based on the position of each of the points composing the contour in the each time phase; and a display controller configured to control a display to display an ultrasonic image based on the ultrasonic image data acquired in the each time phase, for the each time phase, and moreover control the display to display the motion information in the each time phase obtained by the computing part, on each occasion of the each time phase.

A third mode of the present invention is a method for processing an ultrasonic image, comprising: receiving ultrasonic image data acquired for each time phase by scanning a subject with ultrasonic waves, and detecting a contour of a specific tissue based on the ultrasonic image data acquired in a predetermined time phase; obtaining a position of each of points composing the detected contour in the ultrasonic image data acquired in the each time phase, by pattern matching for the each time phase; obtaining motion information indicating a motion state of the specific tissue in the each time phase, based on the position of each of the points composing the contour in the each time phase; and displaying an ultrasonic image based on the ultrasonic image data acquired in the each time phase, and moreover displaying the motion information in the each time phase on each occasion of the each time phase.

A fourth mode of the present invention is A method for processing an ultrasonic image, comprising: receiving ultrasonic image data acquired for each time phase by scanning a subject with ultrasonic waves, and moreover receiving designation of a contour of a specific tissue in an ultrasonic image based on the ultrasonic image data acquired in a predetermined time phase, thereby obtaining a position of each of points composing the designated contour in the ultrasonic image data acquired in the each time phase, by pattern matching for the each time phase; obtaining motion information indicating a motion state of the specific tissue in the each time phase, based on the position of each of the points composing the contour of the each time phase; and displaying an ultrasonic image based on the ultrasonic image data acquired in the each time phase, for the each time phase, and moreover displaying the motion information in the each time phase, on each occasion of the each time phase.

DETAILED DESCRIPTION OF THE EMBODIMENTS

First Embodiment

Figure 1:
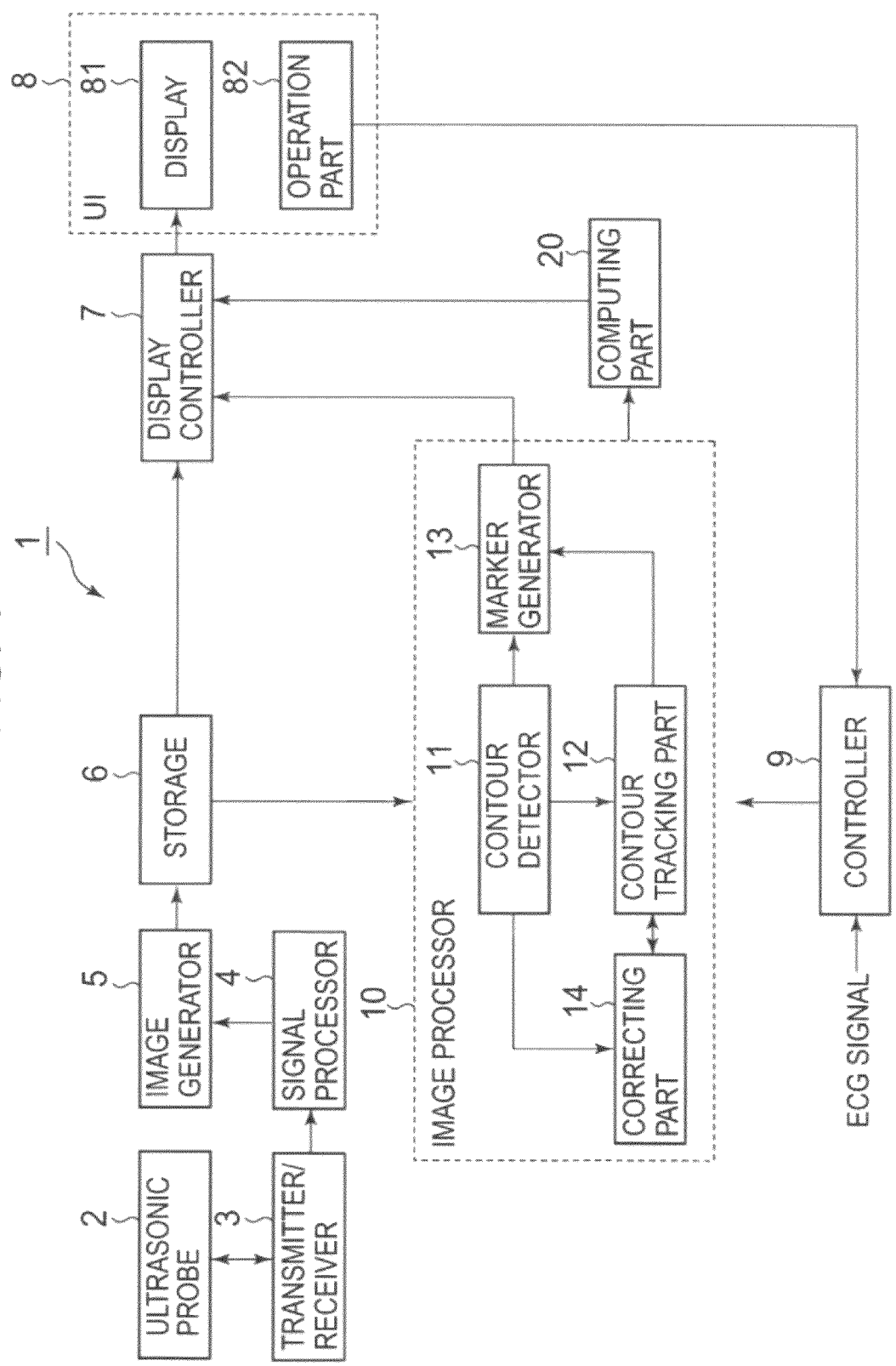
FIG. 1 is a block diagram showing an ultrasonic imaging apparatus according to a first embodiment of the present invention.

An ultrasonic imaging apparatus according to a first embodiment of the present invention will be described with reference to FIG. 1. FIG. 1 is a block diagram showing the ultrasonic imaging apparatus according to the first embodiment of the present invention.

An ultrasonic imaging apparatus 1 comprises: an ultrasonic probe 2; a transmitter/receiver 3; a signal processor 4; an image generator 5; a storage 6; a display controller 7; a user interface (UI) 8; a controller 9; an image processor 10; and a computing part 20. Further, the storage 6, the display controller 7, the user interface (UI) 8, the image processor 10 and the computing part 20 configure an ultrasonic image processing apparatus.

As the ultrasonic probe 2, a 1-dimensional array probe (1D array probe) in which a plurality of ultrasonic transducers are arranged in a row in a predetermined direction (a scanning direction), or a 2-dimensional array probe (2D array probe) in which a plurality of ultrasonic transducers are arranged 2-dimensionally is used. It is also possible to use a 1-dimensional array probe in which ultrasonic transducers are arranged in a predetermined direction (a scanning direction) and the ultrasonic transducers can be mechanically swung in a direction (a swinging direction) orthogonal to the scanning direction.

The transmitter/receiver 3 includes a transmitter and a receiver. The transmitter/receiver 3 supplies electric signals to the ultrasonic probe 2 to generate ultrasonic waves, and receives echo signals received by the ultrasonic probe 2.

The transmitter of the transmitter/receiver 3 is provided with a clock-generating circuit, a transmission delay circuit and a pulsar circuit, which are not illustrated. The clock-generating circuit generates clock signals that determine the transmission timing or transmission frequency of ultrasonic signals. The transmission delay circuit delays the signals at the time of transmission of the ultrasonic waves to execute transmission focus. The pulsar circuit has pulsars of a number equal to the number of individual channels corresponding to the respective ultrasonic transducers, and generates driving pulses at a delayed transmission timing to supply electrical signals to the respective ultrasonic transducers of the ultrasonic probe 2.

The receiver of the transmitter/receiver 3 is provided with a preamplifier circuit, an A/D conversion circuit, a reception delay circuit, and an addition circuit. The preamplifier circuit amplifies echo signals outputted from the respective ultrasonic transducers of the ultrasonic probe 2, for each reception channel. The A/D conversion circuit subjects the amplified echo signals to A/D conversion. The reception delay circuit provides a delay time necessary for determination of the reception directionality with respect to the echo signals after the A/D conversion. The addition circuit adds the delayed echo signals. Reflected components from the direction according to the reception directionality are intensified by the addition. Signals subjected to the addition processing by the transmitter/receiver 3 are sometimes referred to as "RF data (raw data)." The transmitter/receiver 3 outputs the RF data to the signal processor 4.

The signal processor 4 is provided with a B-mode processor, a CFM processor, etc. The B-mode processor performs imaging of the amplitude information of echoes. Specifically, the B-mode processor subjects the received signals having been outputted from the transmitter/receiver 3 to Band Pass Filter processing, and thereafter detects the envelope of the outputted signals. Then, the B-mode processor subjects the detected data to compression processing by logarithmic conversion, thereby imaging the amplitude information of the echoes. Further, the CFM processor conducts imaging of moving blood flow information. This blood flow information includes information such as speed, dispersion and power, and the blood flow information is obtained as binary information.

The image generator 5 converts the data after signal processing into data of a coordinate system based on spatial coordinates (digital scan conversion). For example, the image generator 5 conducts scan conversion processing to the data after signal processing outputted by the B-mode processor to generate B-mode image data (herein sometimes referred to as "tomographic image data") indicating the tissue shape of a subject body. The image generator 5 outputs the ultrasonic image data such as tomographic image data to the storage 6.

Further, in a case where volume scan is performed by the ultrasonic probe 2 and the transmitter/receiver 3, the image generator 5 may receive volume data from the signal processor 4 and subject the volume data to volume rendering, thereby generating 3-dimensional image data sterically representing the tissue. Furthermore, the image generator 5 may subject the volume data to MPR (Multi Plannar Reconstruction) processing, thereby generating image data (MPR image data) at any cross section. The image generator 5 outputs ultrasonic image data such as 3-dimensional image data and MPR image data to the storage 6.

The ultrasonic image data, such as tomographic image data and 3-dimensional image data, generated by the image generator 5 is stored in the storage 6. In a case where an ECG (Electrocardiogram) signal of a subject have been acquired, the controller 9 receives the ECG signal from outside the ultrasonic imaging apparatus 1, and controls the storage 6 to store ultrasonic image data in a state that the cardiac time phase received at timing of generation of the ultrasonic image data is associated thereto.

The ultrasonic imaging apparatus 1 according to the first embodiment scans the heart of a subject with ultrasonic waves, thereby acquiring tomographic image data representing the heart for each cardiac time phase. That is, the ultrasonic imaging apparatus 1 acquires moving image data of the heart. For example, the ultrasonic imaging apparatus 1 scans the heart of a subject with ultrasonic waves for one cardiac cycle or more, thereby acquiring a plurality of tomographic image data (moving image data) for one cardiac cycle or more. Moreover, in a case where the ECG signal has been acquired, the controller 9 controls the storage 6 to store each of the tomographic image data in a state that the cardiac time phase received at timing of generation of the tomographic image data is associated thereto. Consequently, a cardiac time phase at the time of generation of the tomographic image data is associated to each of the plurality of tomographic image data, and the tomographic image data is stored into the storage 6.

The display controller 7 reads in tomographic image data from the storage 6, and controls the display 81 to display tomographic images based on the tomographic image data. For example, when the operator designates any time phase by using an operation part 82, information indicating the designated time phase is outputted to the display controller 7 from the operation part 82. The display controller 7 reads in, from the storage 6, the tomographic image data to which the designated time phase is associated, and controls the display 81 to display tomographic images based on the tomographic image data.

The image processor 10 includes a contour detector 11, a contour tracking part 12, a marker generator 13, and a correcting part 14. The image processor 10 detects the contour of the endocardium of a heart based on the tomographic images representing the heart. The image processor 10 obtains the position of the contour of the endocardium in each cardiac time phase, by executing pattern matching of two tomographic images having been acquired with different cardiac time phases.

The contour detector 11 reads in the tomographic image data from the storage 6, and detects the boundary of the tissue region and the blood region, based on the luminance values of pixels composing the tomographic image data. In the first embodiment, as an example, the contour detector 11 detects a 2-dimensional contour of the endocardium of a heart by using the aforementioned AQ method, based on the tomographic image data. The contour detector 11 reads in, from the storage 6, tomographic image data acquired in a preset cardiac time phase, and detects the 2-dimensional contour of the endocardium based on the luminance distribution of the tomographic image data. The preset cardiac time phase may be changed to any cardiac time phase by the operator. For example, the contour detector 11 reads in, from the storage 6, tomographic image data acquired in end diastole (a cardiac time phase in which an R wave has been detected), or tomographic image data acquired in end systole (a cardiac time phase after a lapse of a predetermined time from the cardiac time phase in which the R wave has been detected), and detects the 2-dimensional contour of the endocardium based on the tomographic image data having been read in. The tomographic image data, to which the cardiac time phase at the time of generation of the tomographic image data is associated, is stored into the storage 6. Therefore, the contour detector 11 reads in, from the storage 6, tomographic image data acquired in a cardiac time phase such as end diastole and end systole, and detects the 2-dimensional contour of the endocardium in the cardiac time phase. Then, the contour detector 11 outputs coordinate information indicating the position of the contour of the detected endocardium to the contour tracking part 12. The 2-dimensional contour of the endocardium detected by the contour detector 11 is set in the contour tracking part 12 as an initial contour of the endocardium to become a tracking object. For example, the 2-dimensional contour of the endocardium in a cardiac time phase in which an R wave has been detected is set in the contour tracking part 12 as the initial contour.

Furthermore, the contour detector 11 may obtain a normal vector at each of the positions on a detected endocardium, and define a position existing outside by a fixed distance in the normal vector direction from each of the positions on the endocardium, as a 2-dimensional contour of the epicardium of a heart. For example, the contour detector 11 defines a position existing 8 mm outside from a position on the endocardium, as the contour of the epicardium. The fixed distance may be changed to any value by the operator. When the 2-dimensional contour of the epicardium is thus detected, the contour detector 11 outputs coordinate information of the contour of the endocardium and coordinate information of the contour of the epicardium to the contour tracking part 12. The 2-dimensional contour of the epicardium detected by the contour detector 11 is set in the contour tracking part 12 as the initial contour of the epicardium to become a tracking object. For example, the contour of the epicardium in a cardiac time phase in which an R wave has been detected is set in the contour tracking part 12 as the initial contour.

Further, the contour detector 11 may detect the 2-dimensional contour of the endocardium and the 2-dimensional contour of the epicardium by using, instead of the AQ method, the ASM (Active Shape Model) method. The method of contour detection by the ASM method is described in, for example, "Active shape models: Their training and application" by Cooles, et al. (Comput. Vis. Image Understand., Vol. 61, No. 1, pp. 38-59, January 1995). In the ASM method, general shapes of a desired tissue are previously registered in a shape dictionary. The contour detector 11 detects the contour of the desired tissue, based on luminance information of tomographic image data and the shapes registered in the shape dictionary. For example, general shapes of the endocardium and epicardium of a heart are previously registered in the shape dictionary. The contour detector 11 detects the contour of the endocardium and the contour of the epicardium based on the luminance information of the tomographic image data and the general shapes of the endocardium and epicardium.

Although the AQ method has an advantage that the processing is relatively easy, it significantly depends on gain setting in contour detection, whereby the result of the detection is easily affected by the gain. Moreover, in the AQ method, there is the risk that not only the endocardium of a heart but also tissues such as papillary muscles and chordae is detected as the contour of the endocardium. On the other hand, the ASM method requires more complicated processing than the AQ method, but is less likely to be affected by the gain setting than the AQ method, and is advantageous in that it is possible to detect the contour of the endocardium excluding papillary muscles and chordae. In the first embodiment, either the AQ method or the ASM method may be used to detect a contour.

As described above, when the 2-dimensional contour of the endocardium (the initial contour of the endocardium) in a predetermined cardiac time phase is detected by the contour detector 11, the contour tracking part 12 performs pattern matching using speckle patterns for two images. Through this pattern matching, the contour tracking part 12 obtains the position of each of points composing the 2-dimensional contour of the endocardium having been set as the initial contour, for each tomographic image data having been generated in each cardiac time phase. That is, the contour tracking part 12 obtains the position of each of the points on the 2-dimensional contour of the endocardium, for each tomographic image data having been generated in each cardiac time phase. Then, the contour tracking part 12 temporally tracks each of the points composing the 2-dimensional contour of the endocardium. In this embodiment, as an example, the contour tracking part 12 temporally tracks each of the points composing the 2-dimensional contour of the endocardium, by using the aforementioned ST method.

For example, the contour tracking part 12 receives coordinate information of each of the points composing the contour of the endocardium having been set as the initial contour, and further reads in, from the storage 6, tomographic image data generated in the following cardiac time phase (may be referred to as "tomographic image data B" hereinafter) after the tomographic image data in which the initial contour has been detected (may be referred to as "tomographic image data A" hereinafter). The contour tracking part 12 performs pattern matching using speckle patterns for two temporally sequential tomographic images, thereby obtaining a motion vector of each of the points composing the contour of the endocardium having been set as the initial contour. That is, the contour tracking part 12 obtains the motion vector of each of the points on the contour of the endocardium, through this pattern matching. To be specific, the contour tracking part 12 performs pattern matching using speckle patterns for the tomographic image A and the tomographic image B, thereby obtaining the motion vector of each of the points composing the contour of the endocardium. This motion vector represents the displacement of each of the points composing the contour and the shift direction in which each of the points has been displaced. That is, the contour tracking part 12 performs pattern matching for two tomographic images, and calculates the shift amount of speckle, thereby obtaining the motion vector of each of the points composing the contour. By obtaining the motion vector of each of the points composing the contour, the position of each of the points composing the contour of the endocardium in the cardiac time phase at the time of generation of the tomographic image data B is obtained.

Furthermore, the contour tracking part 12 reads in, from the storage 6, tomographic image data having been generated in the following cardiac time phase after the tomographic image B (hereinafter, may be referred to as "tomographic image data C"). Then, the contour tracking part 12 performs pattern matching using speckle patterns for the temporally sequential two tomographic images (tomographic image B and tomographic image C), thereby obtaining the motion vector of each of the points composing the contour of the endocardium. Consequently, the position at each of the points composing the contour of the endocardium in the cardiac time phase at the time of generation of the tomographic image C is obtained.

Thus, the contour tracking part 12 obtains the motion vector at each of the points composing the endocardium contour set as the initial contour, for each cardiac time phase at the time of generation of each tomographic image data, by pattern matching using speckles. Consequently, the contour tracking part 12 temporally tracks the motion vector at each of the points composing the contour of the endocardium. As a result, it becomes possible to temporally track each of the points composing the 2-dimensional contour of the endocardium. For example, the contour tracking part 12 obtains the position of each of the points composing the 2-dimensional contour of the endocardium in each cardiac time phase, with respect to all tomographic image data acquired in one cardiac cycle. Consequently, in one cardiac cycle, the position of each of the points composing the 2-dimensional contour of the endocardium in each cardiac time phase is obtained.

Further, when the 2-dimensional contour of the epicardium (the initial contour of the epicardium) in a predetermined cardiac time phase is detected by the contour detector 11, the contour tracking part 12 performs pattern matching using speckle patterns for two images, in the same way as in the tracking of the endocardium. By this pattern matching, the contour tracking part 12 obtains the position of each of the points composing the 2-dimensional contour of the epicardium, in each tomographic image data generated in each cardiac time phase. Then, the contour tracking part 12 temporally tracks each of the points composing the 2-dimensional contour of the epicardium.

As described above, when each of the points composing the 2-dimensional contour of the endocardium in each cardiac time phase is tracked, the computing part 20 receives, from the contour detector 11 and the contour tracking part 12, coordinate information of each of the points composing the 2-dimensional contour of the endocardium in each cardiac time phase, thereby obtaining wall motion information of the endocardium. For example, the computing part 20 obtains the strain (the change ratio of displacement) in the circumferential direction of the endocardium (the tangential direction of the contour) in each cardiac time phase, based on the coordinate information of each of the points composing the 2-dimensional contour of the endocardium in each cardiac time phase. For example, the computing part 20 assumes a cardiac time phase in which an R wave has been detected as a reference time phase, and compares the 2-dimensional contour of the endocardium in the reference time phase with the 2-dimensional contour of the endocardium in another cardiac time phase, thereby obtaining strain in each cardiac time phase. Then, in accordance with the passage of heartbeat, the computing part 20 sets the cardiac time phase of the R wave of the heartbeat to be analyzed, as a new reference time phase, and obtains strain in each cardiac time phase.

For example, the contour detector 11 detects the 2-dimensional contour (the initial contour) of the endocardium in a cardiac time phase in which an R wave has been detected, and outputs the coordinate information of the 2-dimensional contour of the endocardium to the computing part 20. The contour tracking part 12 also outputs the coordinate information of each of the points composing the 2-dimensional contour of the endocardium in each cardiac time phase, to the computing part 20. The computing part 20 receives, from the contour detector 11, the coordinate information of the 2-dimensional contour (the initial contour) of the endocardium in a cardiac time phase in which an R wave has been detected, and further receives, from the contour tracking part 12, the coordinate information of each of the points composing the 2-dimensional contour of the endocardium in each cardiac time phase. Then, the computing part 20 regards the cardiac time phase in which the R wave has been detected as a reference time phase, and obtains the strain in the circumferential direction of the endocardium in each cardiac time phase.

In a case where the 2-dimensional contour of the epicardium in each cardiac time phase has been obtained by the contour detector 11 and the contour tracking part 12, the computing part 20 may obtain the strain in a wall-thickness direction in each cardiac time phase, based on coordinate information of each of the points composing the 2-dimensional contour of the endocardium and coordinate information of each of the points composing the 2-dimensional contour of the epicardium in each cardiac time phase. Herein, the radial strain in the wall-thickness direction is defined as the strain in the thickness direction between the endocardium and the epicardium.

Then, the computing part 20 outputs wall motion information such as strain of the endocardium, to the display controller 7. The display controller 7 receives the wall motion information from the computing part 20, and controls the display 81 to display the wall motion information on each occasion. When the wall motion information in each cardiac time phase is obtained by the computing part 20, the display controller 7 controls the display 81 to display, for each time phase, the wall motion information in each cardiac time phase on each occasion. Besides, for the purpose of enhancement of result stability among heartbeats, the computing part 20 may weight the calculation result for a few heartbeats in the past (including the calculation result for a current heartbeat) to calculate an average value, and the display controller 7 may control the display 81 to display the average value.

Moreover, the computing part 20 may obtain, other than the strain, the displacement or rotational angle of the endocardium or epicardium. Furthermore, the computing part 20 may perform temporal differentiation for strain, displacement, rotational angle or the like to obtain motion information such as the strain rate, velocity or rotation ratio of the endocardium or epicardium. For example, the computing part 20 obtains the difference in strain, displacement or rotation angle in each cardiac time phase, thereby obtaining the strain rate, velocity, rotation rate, or the like. Then, the computing part 20 outputs the strain rate, etc. to the display controller 7. The display controller 7 receives wall motion information such as strain rate in each cardiac time phase from the computing part 20, and controls the display 81 to display the wall motion information in each cardiac time phase on each occasion.

In order to reduce accumulation of errors in tracking by the ST method in accordance with the passage of a plurality of heartbeats, the correcting part 14 corrects the position of the contour of the endocardium to be tracked, at a predetermined timing. In an example (1), the correcting part 14 regularly corrects the position of the contour of the endocardium. To be specific, the correcting part 14 corrects the position of the contour of the endocardium at every N number of heartbeats (N is an integer). In the case of N=1, the correcting part 14 corrects the position of the contour at every heartbeat. That is, the correcting part 14 corrects the position of the contour of the endocardium at a time interval of one heartbeat or more. In an example (2), the correcting part 14 may correct the position of the contour of the endocardium at a timing of instruction by the operator through the operation part 82.

In the example (1), in a case where the position of the contour of the endocardium is regularly corrected, timing for the correction is preset in the controller 9. The controller 9 gives an instruction for the correction to the image processor 10 at the set timing. Following the instruction, the correcting part 14 corrects the position of the contour of the endocardium. For example, every time the controller 9 receives a predetermined number of R waves, the controller 9 gives the instruction for the correction to the image processor 10. In the example (2), when the operator gives an instruction for the correction through the operation part 82, the instruction is outputted to the controller 9, and the controller 9 gives the instruction for the correction to the image processor 10. For example, the operation part 82 is provided with an input device such as a correction execution button. When the operator presses down the button, a signal corresponding to the press is outputted to the controller 9. When receiving the signal, the controller 9 gives the instruction for the correction to the image processor 10.

When the instruction for the correction is given by the controller 9, first, the contour detector 11 executes the AQ method, thereby detecting the 2-dimensional contour of the endocardium. The position (the coordinate) of the 2-dimensional contour detected by the contour detector 11 is defined as a position Paq. Then, at that moment, the position (the coordinate) of each of the points composing the 2-dimensional contour of the endocardium having been obtained by the ST method by the contour tracking part 12 is defined as a position Pst. The correcting part 14 receives coordinate information of the position Paq from the contour detector 11, and further receives coordinate information of the position Pst from the contour tracking part 12, thereby obtaining the position of a new initial contour of the endocardium to be set in the contour tracking part 12, based on the position Paq and the position Pst. For example, the correcting part 14 obtains a position P of the initial contour of the endocardium to be newly set in the contour tracking part 12 by Formula 1 below.

$$\text{Position } P \text{ of initial contour} = \alpha \times Paq + (1-\alpha) \times Pst \quad \text{(Formula 1)}$$

(Herein $0 \leqq \alpha \leqq 1$)

As shown in the above Formula 1, the correcting part 14 adds by weighting the position Paq detected by the contour detector 11 and the position Pst obtained by the contour tracking part 12, thereby obtaining the position P of the initial contour to be newly set in the contour tracking part 12. For example, provided that $\alpha=1$, the position P to be newly set in the contour tracking part 12 is placed to the position Paq newly detected by the contour detector 11.

The correcting part 14 outputs the position P of the initial contour of the endocardium obtained by Formula 1 to the contour tracking part 12. Based on the position P of the initial contour newly obtained, the contour tracking part 12 executes the ST method, thereby tracking the 2-dimensional contour of the endocardium. Moreover, the correcting part 14 may also correct the position of the initial contour of the epicardium through the same process as that for the endocardium.

As described above, the position of the initial contour of the endocardium to be a tracking object and the position of the initial contour of the epicardium to be a tracking object are corrected by the correcting part 14 regularly or at any timing, whereby it is possible to save time and effort for the operator to reset the tracking object, and it becomes possible to obtain wall motion information in real time with high accuracy.

Further, a marker for indicating a 2-dimensional contour of the endocardium may be displayed in the display 81. When receiving coordinate information of the initial contour of the endocardium from the contour detector 11, the marker generator 13 generates a marker for indicating the initial contour. Then, the display controller 7 controls the display 81 to display a tomographic image based on tomographic image data in which the initial contour has been obtained by the contour detector 11, and further controls the display 81 to display the marker for indicating the initial contour in the superimposed state with the tomographic image. A marker for indicating the 2-dimensional contour of the epicardium may also be displayed in the display 81.

Moreover, when receiving, from the contour tracking part 12, the coordinate information of each of the points composing the 2-dimensional contour of the endocardium in each cardiac time phase, the marker generator 13 generates a marker for indicating the 2-dimensional contour of the endocardium in each cardiac time phase is generated. Then, the display controller 7 controls the display 81 to sequentially display tomographic images based on the tomographic image data generated in each cardiac time phase, for each cardiac time phase. Furthermore, the display controller 7 superimposes the marker for indicating the contour of the endocardium in each cardiac time phase with the tomographic image having been generated in each cardiac time phase, and sequentially controls the display 81 to display. Then, the display controller 7 sequentially updates the tomographic image and the marker, and controls the display 81 to display.

Further, in a case where the 2-dimensional contour of the epicardium has been detected by the contour detector 11 and the 2-dimensional contour of the epicardium in each cardiac time phase has been obtained by the contour tracking part 12, the marker generator 13 generates a marker for indicating the 2-dimensional contour of the epicardium, like the marker for indicating the 2-dimensional contour of the endocardium. Then, the display controller 7 superimposes the marker for indicating the contour of the endocardium and the marker for indicating the contour of the epicardium with a tomographic image, and controls the display 81 to display.

Figure 2:
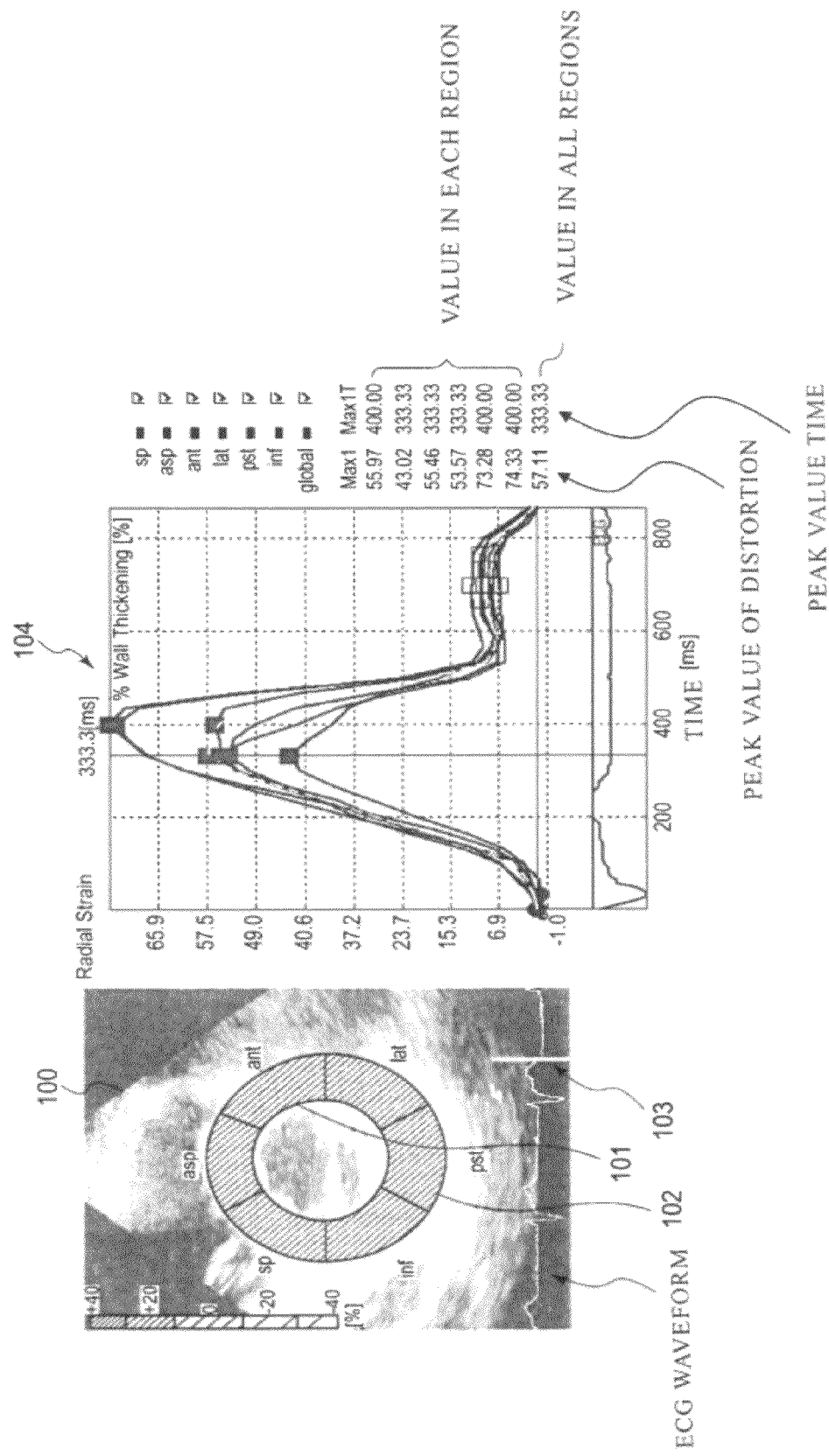
FIG. 2 is a view showing an image acquired by the ultrasonic imaging apparatus according to the first embodiment of the present invention and the result of evaluation of heart function.

FIG. 2 shows an example of the contour of the endocardium, the contour of the epicardium, the motion information and the tomographic image having been obtained in the aforementioned manner. FIG. 2 is a view showing an image acquired by the ultrasonic imaging apparatus according to the first embodiment of the present invention, and wall motion information.

The display controller 7 reads in tomographic image data from the storage 6, and controls the display 81 to display a tomographic image 100 based on the tomographic image data. In the example shown in FIG. 2, the tomographic image 100 represents a short-axis image of a heart. Then, the display controller 7 controls the display 81 to display a marker 101 indicating the contour of the endocardium corresponding to a cardiac time phase at the time of generation of the tomographic image data in the superimposed state with the tomographic image 100. Furthermore, in a case where the contour of the epicardium has been tracked and the marker of the contour has been generated, the display controller 7 controls the display 81 to display a marker 102 indicating the contour of the epicardium in the superimposed state with the tomographic image 100 together with the marker 101. Then, the display controller 7 sequentially updates, for each time phase, the tomographic image 100 having been acquired in each cardiac time phase, the marker 101 indicating the contour of the endocardium and the marker 102 indicating the contour of the epicardium, and controls the display 81 to display. In a case where the contour of the epicardium has not been tracked, the display controller 7 may control the display 81 to display only the marker 101 indicating the contour of the endocardium in the superimposed state with the tomographic image 100.

Furthermore, the display controller 7 controls the display 81 to display, for each cardiac time phase, the wall motion information in each cardiac time phase obtained by the computing part 20. For example, the computing part 20 locally obtains strain in the wall-thickness direction (the direction of thickness between the endocardium and the epicardium) in each cardiac time phase. Then, as shown in FIG. 2, the display controller 7 assigns a color corresponding to the size of the local strain to the region between the endocardium (marker 101) and the epicardium (marker 102), and controls the display 81 to display in the superimposed state with the tomographic image 100. That is, the computing part 20 obtains the strain in the wall-thickness direction in a predetermined location set in advance, and the display controller 7 assigns a color corresponding to the dynamic range of the strain in the predetermined location to the region between the marker 101 and the marker 102, and controls the display 81 to display. Then, the display controller 7 controls the display 81 to display the tomographic image 100 acquired in each cardiac time phase, the marker 100 indicating the contour of the endocardium, the marker 102 indicating the contour of the epicardium and the wall motion information, while sequentially updating for each time phase.

Further, as shown in FIG. 2, the computing part 20 may set the position of the center of gravity in a short-axis image of a heart and draw straight lines radially from the position of the center of gravity, thereby dividing the short-axis image into six regions, as recommended by the ASE (American Society of Echocardiography). In this case, the computing part 20 obtains strain at a plurality of locations included in each of the regions and obtains the average value of the strain at the plurality of the locations, thereby obtaining the average value of the strain in each of the regions. In the example shown in FIG. 2, the computing part 20 divides the tomographic image 100 equivalent to the short-axis image into six regions inf (inferior wall): D1; pst (posterior wall): D2; lat (lateral wall): D3; ant (anterior wall): D4; asp (anterior-septum): D5; sp (septum): D6. The computing part 20 obtains the average value of the size of the strain in the wall-thickness direction (the direction of thickness between the endocardium and the epicardium) in each of the regions D1-D6.

For example, the computing part 20 obtains, for each region, the peak value (Max1 in FIG. 2) of the strain in one heartbeat and the time (Max1T in FIG. 2) from the cardiac time phase in which an R wave of a reference time phase is detected to the cardiac time phase in which the peak value is obtained, and outputs the values to the display controller 7. The display controller 7 controls the display 81 to display the peak value (Max1) of the strain and the time (Max1T) to obtain the peak value.

Further, the computing part 20 may show temporal change of the average value of the strain in each of the regions with a graph. The display controller 7 receives graph data showing the temporal change of the average value of the strain from the computing part 20, and controls the display 81 to display the graph. For example, as shown in FIG. 2, the display controller 7 controls the display 81 to display a graph 104 created by the computing part 20 and showing the temporal change of the average value of the strain in each of the regions. In the graph 104 in FIG. 2, the horizontal axis indicates time (ins) and the vertical axis indicates strain (Radial Strain).

Moreover, the computing part 20 may generate an average value of strain in all the regions or graph data showing temporal change of the average value. The display controller 7 controls the display 81 to display the average value of the strain in all the regions or the graph. For example, "global" in FIG. 2 represents the average value of the strain in all the regions.

Moreover, the display controller 7 may control the display 81 to display an ECG wave, and control the display 81 to display a bar 103 indicating a cardiac time phase in which a tomographic image displayed in the display 81 has been acquired, in the superimposed state with the ECG wave. Then, the display controller 7 moves the bar 103 on the ECG wave, and controls the display 81 to display the tomographic image 100, marker 101, marker 102 and graph 104 in the cardiac time phase indicated by the bar 103. As described above, the display controller 7 controls the display 81 to display the tomographic image 100 and the graph 104 while updating in accordance with the cardiac time phase.

The user interface (UI) 8 includes the display 81 and the operation part 82. The display 81 is composed of a monitor such as a CRT and a liquid crystal display, and displays a tomographic image or a 3-dimensional image on a screen thereof. The operation part 82 is composed of a keyboard, a mouse, a trackball, a TCS (Touch Command Screen) or the like, and various kinds of instructions are given thereto through operations by the operator. For example, an instruction on the timing for correcting the initial contour of the endocardium or epicardium is given by using the operation part 82.

The controller 9 is connected to the respective parts of the ultrasonic imaging apparatus 1, and controls the operations of the respective parts.

Further, the image processor 10 includes a CPU (Central Processing Unit) and a storage (not illustrated) such as a ROM (Read Only Memory), RAM (Random Access Memory) and an HDD (Hard Disk Drive). The storage stores image-processing programs for executing the functions of the respective parts of the image processor 10. The image-processing programs include a contour detection program for executing the function of the contour detector 11, a contour-tracking program for executing the function of the contour tracking part 12, a marker-generating program for executing the function of the marker generator 13, and a correction program for executing the function of the correcting part 14. When the CPU executes the contour-detecting program, the contour of the endocardium (epicardium) of the heart is detected from tomographic image data. When the CPU executes the contour-tracking program, the contour of the endocardium (epicardium) in each cardiac time phase is obtained. When the CPU executes the marker-generating program, a marker for indicating the contour of the endocardium (epicardium) is generated. When the CPU executes the correction program, the position of the contour of the endocardium (epicardium) is corrected at a pre-set timing or at a timing of reception of an instruction from the operator.

Further, the computing part 20 includes a CPU and a storage (not illustrated) such as a ROM, a RAM and an HDD. The storage stores a computing program for executing the function of the computing part 20. When the CPU executes the computing program, wall motion information such as strain and displacement of the endocardium (or epicardium) is obtained.

Moreover, the display controller 7 includes a CPU and a storage (not illustrated) such as a ROM, a RAM and an HDD. The storage stores a display control program for executing the function of the display controller 7. When the CPU executes the display control program, tomographic images, markers and wall motion information are displayed in the display 81.

As described above, by detecting the initial contour of the endocardium and the initial contour of the epicardium, and temporally tracking the contour by pattern matching, setting of the initial contour for tracking the contour is automated. Consequently, it becomes possible to obtain and display the wall motion information in real time.

(Ultrasonic Image Processing Apparatus)

Further, an ultrasonic image processing apparatus for tracking the contour of the endocardium to obtain wall motion information may be provided outside an ultrasonic imaging apparatus. This ultrasonic image processing apparatus comprises the storage 6, the display controller 7, the user interface 8, the image processor 10 and the computing part 20, which are described above. The ultrasonic image processing apparatus acquires a plurality of tomographic image data whose acquisition times are sequential, from the external ultrasonic imaging apparatus, and obtains wall motion information by tracking the contour of the endocardium and the contour of the epicardium based on the plurality of tomographic image data.

The ultrasonic imaging apparatus provided outside the ultrasonic image processing apparatus scans the heart with ultrasonic waves, whereby the tomographic image data is acquired for each cardiac time phase. The ultrasonic image processing apparatus receives a plurality of tomographic image data acquired by the ultrasonic imaging apparatus, and stores the plurality of tomographic image data into the storage 6. The image processor 10 of the ultrasonic image processing apparatus detects the 2-dimensional contour of the endocardium and the 2-dimensional contour of the epicardium by the AQ method or the like. Moreover, the image processor 10 tracks the contour of the endocardium by obtaining the position of each of the points composing the 2-dimensional contour of the endocardium in each cardiac time phase by the ST method. Likewise, the tracking is performed for the epicardium. The computing part 20 of the ultrasonic image processing apparatus obtains wall motion information such as strain and displacement, based on the position of each of the points composing the 2-dimensional contour having been tracked by the image processor 10.

As described above, the ultrasonic image processing apparatus provided outside the ultrasonic imaging apparatus detects and tracks the contour of the endocardium and the contour of the epicardium in each cardiac time phase, thereby being capable of obtaining and displaying wall motion information in real time in the same manner as the aforementioned ultrasonic imaging apparatus 1.

(Operation)

Figure 3:
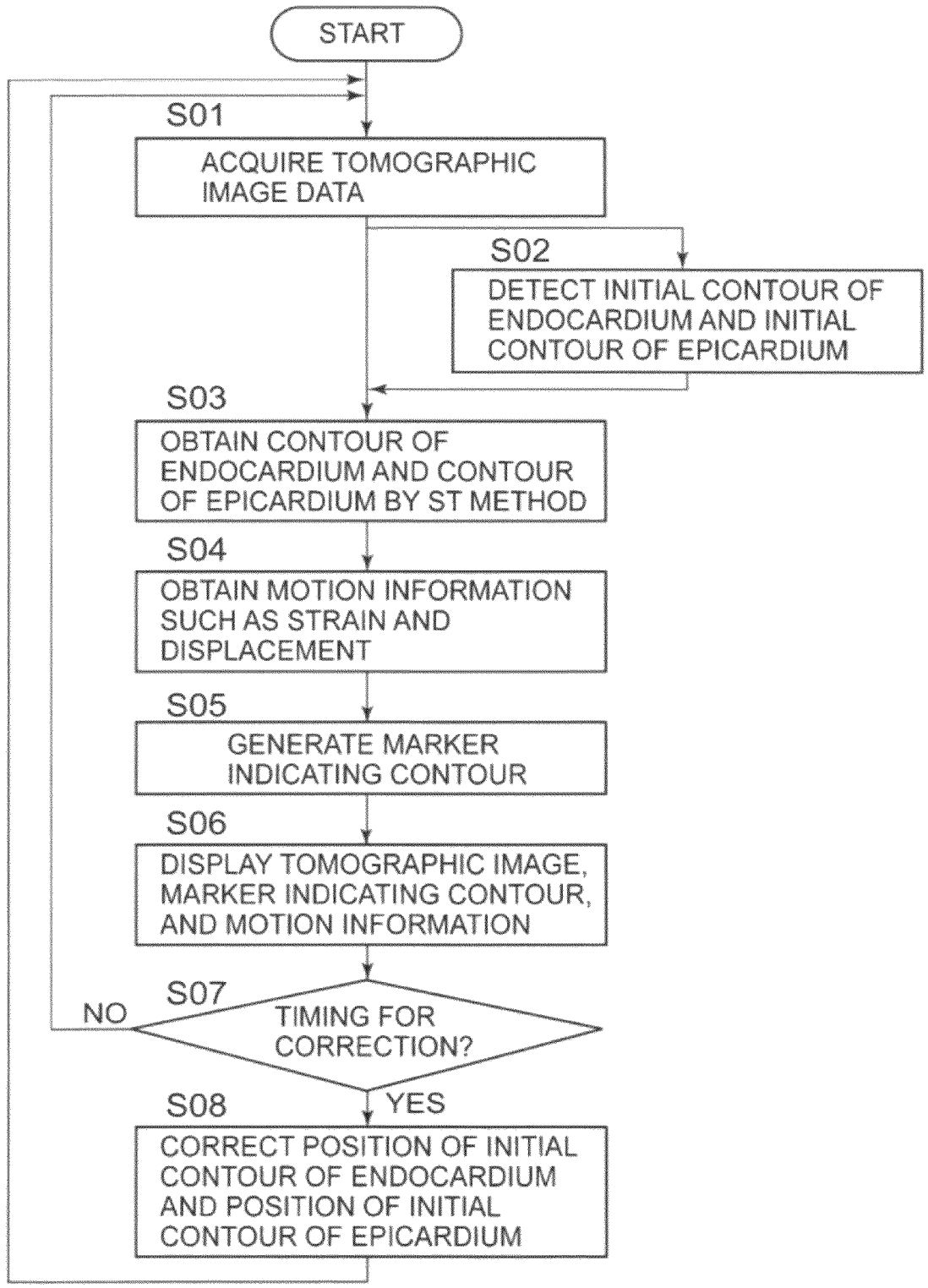
FIG. 3 is a flow chart showing a series of operations of the ultrasonic imaging apparatus according to the first embodiment of the present invention.

Next, the operations of the ultrasonic imaging apparatus (ultrasonic image processing apparatus) according to the first embodiment of the present invention will be described with reference to FIG. 3. FIG. 3 is a flowchart for explaining a series of operations by the ultrasonic imaging apparatus according to the first embodiment of the present invention. In this embodiment, a heart is a site to diagnose, a plurality of tomographic image data (moving image data) acquired at different times are acquired, and the 2-dimensional contour of endocardium and the 2-dimensional contour of epicardium of the heart for evaluation of heart function are detected based on the tomographic image data.

(Step S01)

First, the ultrasonic probe 2 is applied to a subject to transmit ultrasonic waves to the heart, and tomographic image data (moving image data of the heart) in each cardiac time phase is generated by the image generator 5. The controller 9 receives an ECG signal from outside the ultrasonic imaging apparatus 1, and controls the storage 6 to store the generated tomographic image data in association with the cardiac time phase in which the tomographic image data has been generated.

(Step S02)

The contour detector 11 reads in, from the storage 6, the tomographic image data having been acquired in a preset cardiac time phase (for example, a cardiac time phase in which an R wave has been detected), and detects the 2-dimensional contour of the endocardium and the 2-dimensional contour of the epicardium of the heart based on luminance distribution of the tomographic image data. The 2-dimensional contour of the endocardium and the 2-dimensional contour of the epicardium detected by the contour detector 11 are set as the initial contours into the contour tracking part 12.
(Step S03)

The contour tracking part 12 reads in, from the storage 6, tomographic image data acquired in a cardiac time phase after that of the tomographic image data in which the initial contour has been obtained, and performs pattern matching using speckle patterns for the two images. Through this pattern matching, the contour tracking part 12 obtains the position of each of the points composing the 2-dimensional contour of the endocardium and the position of each of the points composing the 2-dimensional contour of the epicardium in the cardiac time phase.
(Step S04)

The computing part 20 receives coordinate information of each of the points composing the 2-dimensional contour of the endocardium and coordinate information of each of the points composing the 2-dimensional contour of the epicardium in the cardiac time phase, and obtains wall motion information such as strain and displacement in the cardiac time phase based on the coordinate information.
(Step S05)

The marker generator 13 receives coordinate information of each of the points composing the 2-dimensional contour of the endocardium and coordinate information of each of the points composing the 2-dimensional contour of the epicardium in the cardiac time phase, and generates a marker indicating the contour of the endocardium and a marker indicating the contour of the epicardium.
(Step S06)

The display controller 7 controls the display 81 to display a tomographic image based on the tomographic image data generated in the cardiac time phase. Furthermore, the display controller 7 controls the display 81 to display the marker indicating the 2-dimensional contour of the endocardium and the marker indicating the 2-dimensional contour of the epicardium in the superimposed state with the tomographic image. Moreover, the display controller 7 controls the display 81 to display the wall motion information obtained by the computing part 20.
(Steps S07, S08)

In a case where it is the timing for correcting the position of the initial contour (Step S07, Yes), the controller 9 gives an instruction for correcting to the image processor 10. For example, the timing for correcting the position of the initial contour is preset in the controller 9, and the controller 9 gives an instruction for correcting to the image processor 10 at the timing. The operator may give an instruction for correcting by using the operation part 82. The correcting part 14 obtains the position of a new initial contour for the endocardium and the epicardium in accordance with the aforementioned Formula 1 (Step S08). The initial contour obtained by the correcting part 14 is set into the contour tracking part 12, and the contour tracking part 12 tracks the contour indicated by the initial contour. The processes of Step S01 and Steps S03-S06 are repeated, whereby the 2-dimensional contour of the endocardium and the 2-dimensional contour of the epicardium are tracked, and the wall motion information in each cardiac time phase is obtained.

On the other hand, in a case where it is not the timing for correcting the position of the initial contour (Step S07, No), the processes of Step S01 and Steps S03-S06 are repeated, whereby the 2-dimensional contour of the endocardium and the 2-dimensional contour of the epicardium are tracked, and the wall motion information in each cardiac time phase is obtained.
(Modification)

Figure 4:
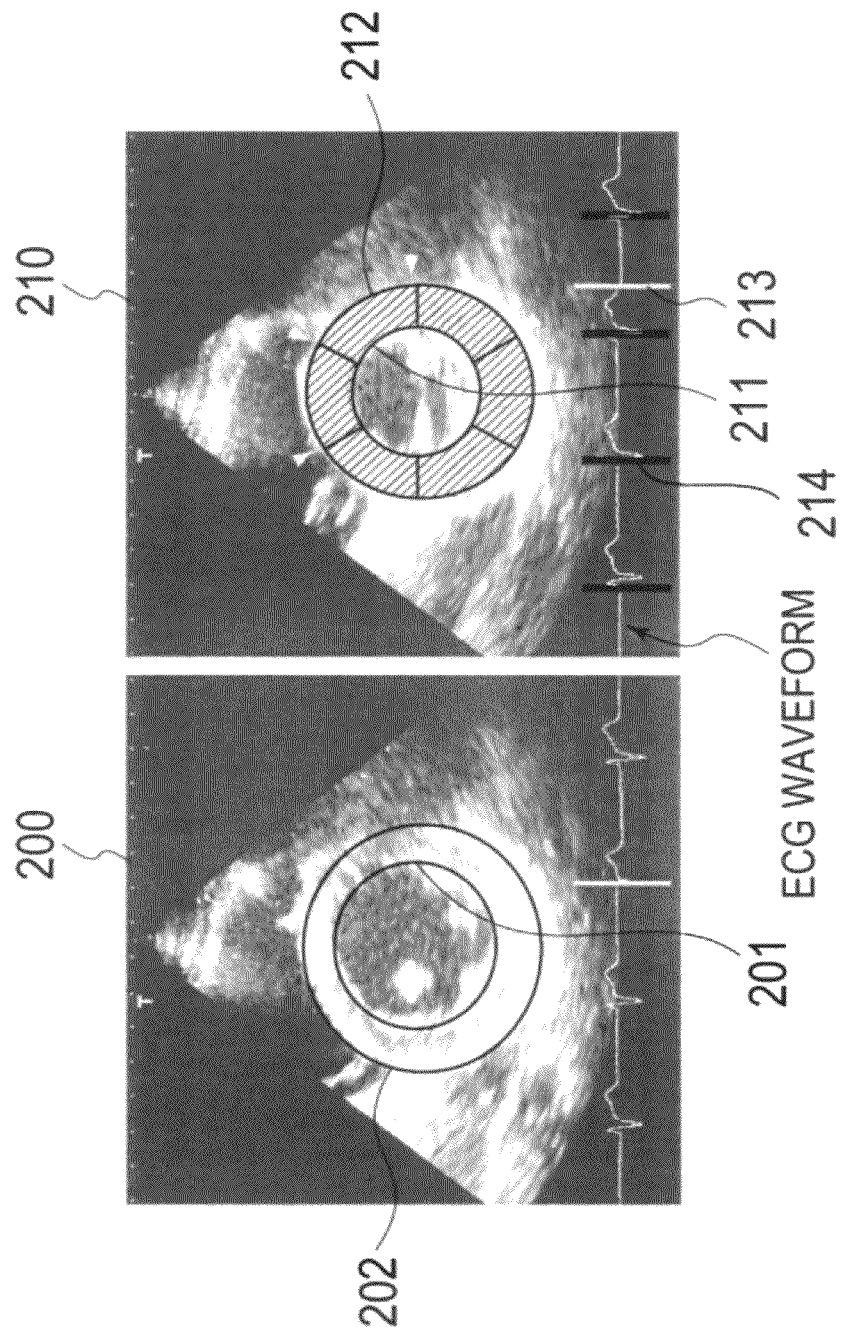
FIG. 4 is a view showing images acquired by an ultrasonic imaging apparatus according to a modification.

Next, a modification of the aforementioned first embodiment will be described with reference to FIG. 4. FIG. 4 is a view showing images acquired by an ultrasonic imaging apparatus according to the modification. In the aforementioned first embodiment, the contour detector 11 detects the initial contour of the endocardium and the initial contour of the epicardium based on tomographic image data. In this modification, the operator designates the initial contour of the endocardium and the initial contour of the epicardium. That is, the contour tracking part 12 receives designation of the 2-dimensional contour of the endocardium in a tomographic image acquired in a predetermined cardiac time phase, and obtains the position of each of the points composing the 2-dimensional contour of the endocardium in each cardiac time phase by pattern matching for each cardiac time phase. Likewise, the contour tracking part 12 receives designation of the 2-dimensional contour of the epicardium, and obtains the position of each of the points composing the 2-dimensional contour of the epicardium in each cardiac time phase.

In the modification, the display controller 7 controls the display 81 to display a tomographic image for setting an initial contour and a tomographic image for displaying motion information side by side. For example, as shown in FIG. 4, the display controller 7 reads in, from the storage 6, tomographic image data acquired in a preset cardiac time phase, and controls the display 81 to display a tomographic image 200 based on the tomographic image data. In the example shown in FIG. 4, the tomographic image 200 represents a short-axis image of a heart. For example, the display controller 7 reads in, from the storage 6, the tomographic image data acquired in end diastole (a cardiac time phase in which an R wave has been detected) or tomographic image data acquired in end systole, and controls the display 81 to display a tomographic image based on the tomographic image data. Furthermore, the display controller 7 controls the display 81 to display the tomographic image 200 while updating in a preset cycle. For example, the display controller 7 controls the display 81 to display the tomographic image 200 while updating at a time interval of one heartbeat or more. In one example, the display controller 7 reads in tomographic image data acquired in a cardiac time phase in which an R wave has been detected, from the storage 6 for each heartbeat, and updates the tomographic image 200 to control the display 81 to display. The tomographic image 200 is an image used for setting the initial contour of the endocardium and the initial contour of the epicardium, and is equivalent to one example of the "tomographic image for initial contour setting" of the present invention.

The operator designates the initial contour of the endocardium and the initial contour of the epicardium while observing the tomographic image. For example, the operator designates the initial contour of the endocardium by tracing the 2-dimensional contour of the endocardium shown in the tomographic image 200 by using the operation part 82. Furthermore, the operator designates the initial contour of the epicardium by tracing the 2-dimensional contour of the epicardium shown in the tomographic image 200 by using the operation part 82. Once the contour of the endocardium and the contour of the epicardium are thus designated, coordinate information of the 2-dimensional contour of the endocardium and coordinate information of the 2-dimensional contour of the epicardium are outputted to the image processor 10 from the user interface (UI) 8 via the controller 9. The marker generator 13 generates a marker for indicating the initial contour of the endocardium based on the coordinate information of the 2-dimensional contour of the endocardium designated by the operator. Likewise, the marker generator 13 generates a marker for indicating the initial contour of the epicardium based on the coordinate information of the 2-dimensional contour of the epicardium. When receiving the marker indicating the initial contour, the display controller 7 controls the display 81 to display the marker in the superimposed state with the tomographic image 200. In the example shown in FIG. 4, the display controller 7 controls the display 81 to display a marker 201 indicating the initial contour of the endocardium and a marker 202 indicating the initial contour of the epicardium in the superimposed state with the tomographic image 200. Thus, the contour of the endocardium and the contour of the epicardium designated by the operator are set in the contour tracking part 13 as the initial contours.

The display controller 7 may control the display 81 to display a contour setting marker for setting an initial contour so as to be superimposed with the tomographic image 200. For example, the display controller 7 controls the display 81 to display a circular marker or an oval-shaped marker having a preset size so as to be superimposed with the tomographic image 200. The operator moves the contour setting maker to a desired position on the screen by using the operation part 82, thereby designating the initial contour of the endocardium and the initial contour of the epicardium. For example, the operator moves the contour setting marker to a position substantially matching the shape of the contour setting marker, thereby designating the initial contour of the endocardium and the initial contour of the epicardium.

Further, in a case where an apex approach image of a heart is acquired and displayed in the display 81, the operator may designate the position of the apex and the position of both annuluses by using the operation part 82 so that the contour tracking part 12 estimates the position of the 2-dimensional contour of the endocardium and the position of the 2-dimensional contour of the epicardium based on the three designated points. The contour tracking part 12 temporally tracks the contour of the endocardium and the contour of the epicardium having been estimated, by pattern matching. It is also possible to register the shapes of the annuluses in a shape dictionary in advance and estimate the 2-dimensional contour of the endocardium and the 2-dimensional contour of the epicardium through self-retrieval type processing using pattern matching. In this case, the operator needs to designate only the position of the apex, so that it is possible to reduce the burden of the operator.

As described above, when the operator designates the initial contour of the endocardium and the initial contour of the epicardium, the contour tracking part 12 tracks the 2-dimensional contour of the endocardium and the 2-dimensional contour of the epicardium by the ST method, as in the first embodiment. Then, the marker generator 13 generates a marker indicating the 2-dimensional contour of the endocardium and a marker indicating the 2-dimensional contour of the epicardium in each cardiac time phase. The display controller 7 reads in, from the storage 6, tomographic image data acquired in each cardiac time phase, and controls the display 81 to sequentially display, for each cardiac time phase, tomographic images based on the tomographic image data in each cardiac time phase. Furthermore, the display controller 7 receives, from the marker generator 13, the marker indicating the contour of the endocardium and the marker indicating the contour of the epicardium in each cardiac time phase, and controls the display 81 to sequentially display, for each cardiac time phase, the markers in each cardiac time phase in the superimposed state with the tomographic image. For example, as shown in FIG. 4, the display controller 7 controls the display 81 to sequentially display, for each cardiac time phase, a tomographic image 210 in each cardiac time phase, and then controls the display 81 to sequentially display a marker 211 indicating the contour of the endocardium in each cardiac time phase in the superimposed state with the tomographic image 210. Moreover, the display controller 7 controls the display 81 to sequentially display, for each cardiac time phase, a marker 212 indicating the contour of the epicardium in each cardiac time phase in the superimposed state with the tomographic image 210. In the example shown in FIG. 4, the display controller 7 controls the display 81 to display the tomographic image 200 for setting an initial contour while updating in a preset cycle. Moreover, the display controller 7 controls the display 81 to sequentially display the tomographic image 210 side by side with the tomographic image 200, for each cardiac time phase.

Furthermore, the display controller 7 may control the display 81 to display an ECG wave, and control the display 81 to display a bar 213 indicating the current cardiac time phase in which tomographic image data displayed in the display 81 has been acquired, in the superimposed state with the ECG wave. The display controller 7 then moves the bar 213 on the ECG wave, and controls the display 81 to display the tomographic image 210, marker 211 and marker 212 in the cardiac time phase indicated by the bar 213. The bars 214 on the ECG wave show the timing of acquisition of tomographic image 200 for initial contour setting.

As in the above first embodiment, the computing part 20 obtains wall motion information such as strain or displacement in each cardiac time phase, based on coordinate information of each of the points composing the 2-dimensional contour of the endocardium and coordinate information of each of the points composing the 2-dimensional contour of the epicardium in each cardiac time phase. The display controller 7 controls the display 81 to display, for each cardiac time phase, wall motion information in each cardiac time phase.

In addition, the initial contour of the endocardium and the initial contour of the epicardium may be set again at any time. As in the abovementioned method for designating an initial contour, the operator designates, at any time, the contour of the endocardium and the contour of the epicardium on the tomographic image 200 for initial contour setting displayed in the display 81 by using the operation part 82. As described above, when the initial contour of the endocardium and the initial contour of the epicardium are designated again, coordinate information of the newly designated initial contour is outputted to the image processor 10 from the user interface (UI) 8. The contour tracking part 12 tracks the contour of the endocardium and the contour of the epicardium, which have been newly designated.

Also in a case where an initial contour is set again, the display 7 may control the display 81 to display a contour setting marker for designating the initial contour in the superimposed state with the tomographic image 200. At this moment, the display controller 7 may control the display 81 to display a marker indicating the contour of the endocardium in a predetermined cardiac time phase obtained by the contour tracking part 12, as the contour setting marker in the superimposed state with the tomographic image 200. This contour setting maker is generated by the marker generator 13. Thus, by generating the contour setting maker based on the contour of the endocardium obtained by the ST method, it becomes possible to match the shape of the contour setting maker with the position or contour of an actual myocardium. For the epicardium, designation by a contour setting maker may be performed.

The display controller 7 may control the display 81 to display the tomographic image 200 for initial contour setting at all times. Alternatively, the display controller 7 may control the display 81 to display the tomographic image 200 only when setting an initial contour. For example, when the operator gives an instruction to set an initial contour by using the operation part 82, the display controller 7 reads in tomographic image data acquired in a preset cardiac time phase (for example, a cardiac time phase in which an R wave has been detected), from the storage 6, and controls the display 81 to display the tomographic image 200 based on the tomographic image data, as a tomographic image for initial contour setting. Then, when an initial contour is designated by the operator, the display controller 7 controls the display 81 to display only the tomographic image 210 for displaying wall motion information.

The display controller 7 may control the display 81 to display the tomographic image 210 of each cardiac time phase, for each cardiac time phase, and control the display 81 to display the tomographic image 200 for initial contour setting acquired in a preset cardiac time phase, at a predetermined timing, instead of the tomographic image 210. At this moment, the display controller 7 controls the display 81 to display the tomographic image 200 while updating at time intervals of one heartbeat or more. Then, by using the operation part 82, the operator designates the contour of the endocardium and the contour of the epicardium on the tomographic image 200 for initial contour setting displayed in the display 81. When the initial contour is designated by the operator, the display controller 7 controls the display 81 to display the tomographic image 210 of each cardiac time phase, for each cardiac time phase, instead of the tomographic image 200.

In this modification, since the operator designates the initial contour of the endocardium and the initial contour of the epicardium, the image processor 10 may be configured without the contour detector 11.

Also, as in the above first embodiment, the ultrasonic image processing apparatus may be provided outside the ultrasonic imaging apparatus.

Second Embodiment

Figure 5:
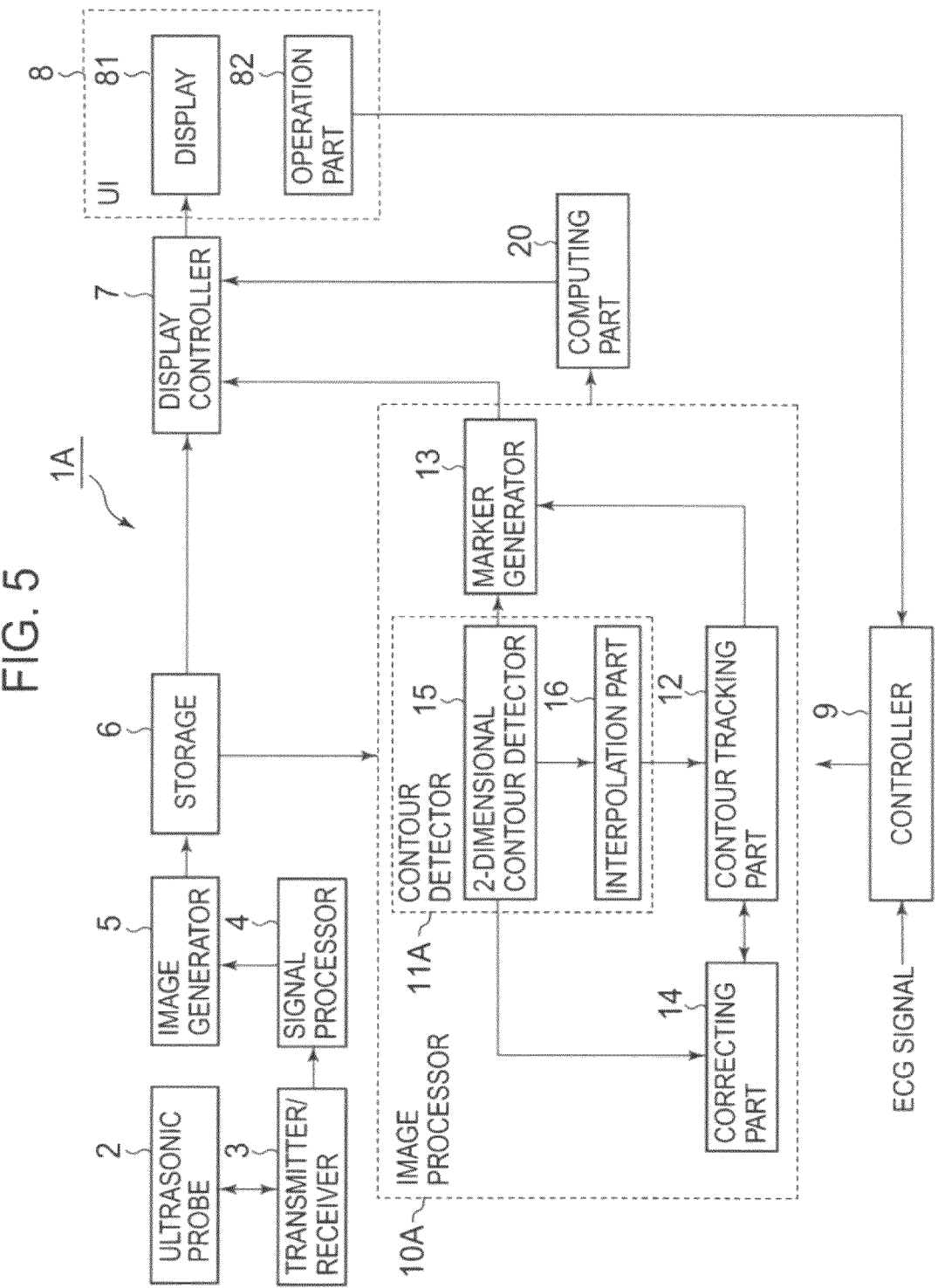
FIG. 5 is a block diagram showing an ultrasonic imaging apparatus according to a second embodiment of the present invention.
Figure 6A:
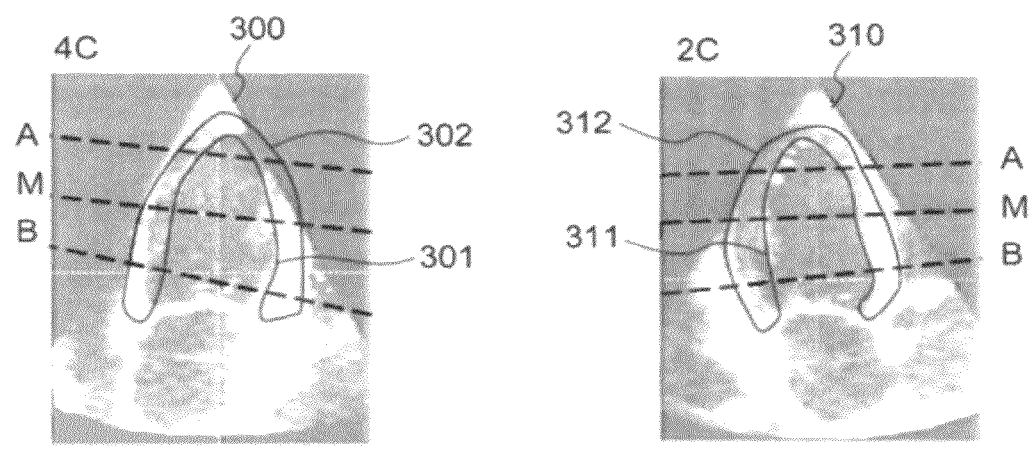
FIG. 6A is a view showing images acquired by the ultrasonic imaging apparatus according to the second embodiment of the present invention.
Figure 6B:
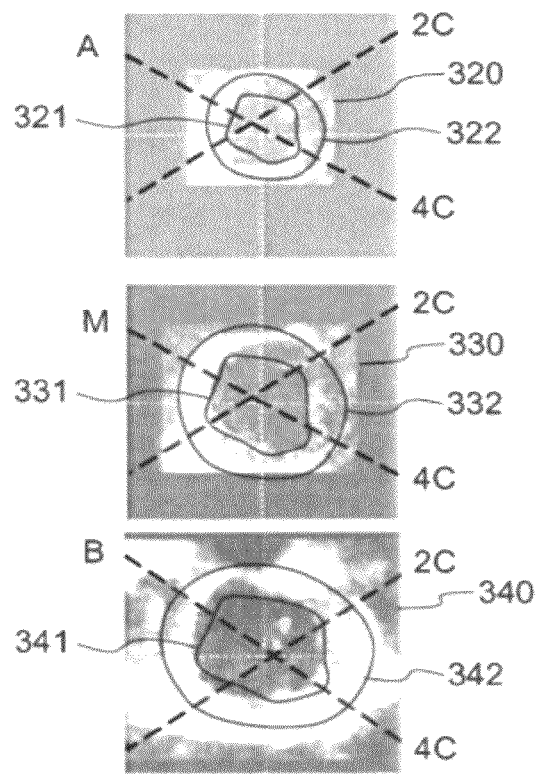
FIG. 6B is a view showing images acquired by the ultrasonic imaging apparatus according to the second embodiment of the present invention.

Next, the ultrasonic imaging apparatus according to a second embodiment of the present invention will be described referring to FIGS. 5, 6A and 6B. FIG. 5 is a block diagram showing the ultrasonic imaging apparatus according to the second embodiment of the present invention. FIGS. 6A and 6B are views showing images acquired by the ultrasonic imaging apparatus according to the second embodiment of the present invention.

In the aforementioned first embodiment, wall motion information is obtained by tracking the contour of the endocardium and the contour of the epicardium on a 2-dimensional plane based on tomographic image data of a 2-dimensional image. In the second embodiment, wall motion information is obtained by tracking a 3-dimensional contour of the endocardium and a 3-dimensional contour of the epicardium based on volume data of a 3-dimensional image.

An ultrasonic imaging apparatus 1A according to the second embodiment comprises an image processor 10A instead of the image processor 10 of the ultrasonic imaging apparatus 1 according to the first embodiment. The image processor 10A includes a contour detector 11A, the contour tracking part 12, the marker generator 13, and the correcting part 14.

In the second embodiment, volume data is acquired for each cardiac time phase by performing volume scan using a 2-dimensional array probe as the ultrasonic probe 2. Then, the image generator 5 subjects the volume data acquired in a preset cardiac time phase (for example, a cardiac time phase in which an R wave has been detected) to MPR processing, thereby generating MPR image data at any cross section. For example, the image generator 5 subjects the volume data to the MPR processing, thereby obtaining the MPR image data at a plurality of different cross sections, for each of the cross sections. In one example, the image generator 5 generates two MPR image data at cross sections orthogonal to each other. For example, as shown in FIG. 6A, the image generator 5 generates an Apical 4 Chamber image (4C) 300 and an Apical 2 Chamber image (2C) 310 along the long-axis direction of a heart. The cross sections may be previously set in the image generator 5, or may be designated by the operator using the operation part 82. The MPR image data generated by the image generator 5 is stored in the storage 6. The display controller 7 may read in the MPR image data stored in the storage 6 and control the display 81 to display the MPR image based on the MPR image data. For example, the display controller 7 may control the display 81 to display the Apical 4 Chamber image (4C) 300 and the Apical 2 Chamber image (2C) 310.

The contour detector 11A includes a 2-dimensional contour detector 15 and an interpolation part 16. The 2-dimensional contour detector 15 reads in a plurality of MPR image data acquired in a preset cardiac time phase (for example, a cardiac time phase in which an R wave has been detected), from the storage 6, and detects the 2-dimensional contour of the endocardium and the 2-dimensional contour of the epicardium, from the respective MPR image data by the AQ method or the ASM method. In the example shown in FIG. 6A, the 2-dimensional contour detector 15 detects a 2-dimensional contour 301 of the endocardium and a 2-dimensional contour 302 of the epicardium from the Apical 4 Chamber image (4C) 300. Further, the 2-dimensional detection part 15 detects a 2-dimensional contour 311 of the endocardium and a 2-dimensional contour 312 of the epicardium from the Apical 2 Chamber image (2C) 310. Thus, in the one example of the second embodiment, the 2-dimensional contour of the endocardium and the 2-dimensional contour of the epicardium in the long-axis direction are detected based on the MPR image data along the long-axis direction of the heart. Then, the contour detector 11 outputs coordinate information indicating the position of the 2-dimensional contour of the endocardium and coordinate information indicating the position of the 2-dimensional contour of the epicardium, to the interpolation part 16.

Based on the 2-dimensional contour 301 of the endocardium obtained from the Apical 4 Chamber image (4C) 300 and the 2-dimensional contour 311 of the endocardium obtained from the Apical 2 Chamber image (3C) 310, the interpolation part 16 spatially interpolates the contour of the endocardium by using a spline function or the like, thereby obtaining the position of the 3-dimensional contour of the endocardium. Further, based on the 2-dimensional contour 302 of the epicardium obtained from the Apical 4 Chamber image (4C) 300 and the 2-dimensional contour 312 of the epicardium obtained from the Apical 2 Chamber image (3C) 310, the interpolation part 16 spatially interpolates the contour of the epicardium by using a spline function or the like, thereby obtaining the position of the 3-dimensional contour of the epicardium. That is, the interpolation part 16 obtains the position of the contour of the endocardium at each cross section (each C plane) along a direction orthogonal to the long-axis direction (i.e., the short-axis direction), thereby obtaining the position of the 3-dimensional contour of the endocardium. Likewise, the interpolation part 16 obtains the position of the contour of the epicardium at each C plane along the short-axis direction, thereby obtaining the position of the 3-dimensional contour of the epicardium.

As described above, the interpolation part 16 obtains the position of the 3-dimensional contour of the endocardium at each depth in the long-axis direction, based on the contour 301 and the contour 311 defined at cross sections along the long-axis direction. Through this process, the position of the 3-dimensional contour of the endocardium is obtained. Likewise, the interpolation part 16 obtains the position of the contour of the epicardium at each depth in the long-axis direction, based on the contour 302 and the contour 312 defined at cross sections along the long-axis direction. Through this process, the position of the 3-dimensional contour of the epicardium is obtained. Coordinate information indicating the position of the 3-dimensional contour of the endocardium and coordinate information indicating the position of the 3-dimensional contour of the epicardium are outputted to the contour tracking part 12 from the interpolation part 16, and are set in the contour tracking part 12 as the initial contour of the endocardium and the initial contour of the epicardium, respectively.

The image generator 5 may generate MPR image data of a cross section along the long-axis direction and further generate MPR image data of a cross section (C plane) along the direction orthogonal to the long-axis direction (i.e., the short-axis direction). For example, as shown in 6A, the image generator 5 generates the Apical 4 Chamber image (4C) 300 and the Apical 2 Chamber image (2C) 310 along the long-axis direction of the heart. Furthermore, as shown in FIG. 6B, the image generator 5 generates an MPR image 320 at a cross section along a line A at a predetermined depth in the long-axis direction. Likewise, the image generator 5 generates an MPR image 330 at a cross section along a line M at a predetermined depth. Likewise, the image generator 5 generates an MPR image 340 at a cross section along a line B at a predetermined depth. The MPR image data generated by the image generator 5 is stored in the storage 6. The cross sections designated by the lines A, M and B, respectively, may be previously set in the image generator 5, or the cross sections may be designated by the operator using the operation part 82.

The 2-dimensional contour detector 15 reads in the MPR image data at each cross section acquired in a preset cardiac time phase (for example, a cardiac time phase in which an R wave has been detected), from the storage 6, and detects the 2-dimensional contour of the endocardium and the 2-dimensional contour of the epicardium at each cross section. For example, the 2-dimensional contour detector 15 detects the 2-dimensional contour 301 of the endocardium and the 2-dimensional contour 302 of the epicardium, based on the Apical 4 Chamber image (4C) 300 along the long-axis direction. Further, the 2-dimensional contour detector 15 detects the 2-dimensional contour 311 of the endocardium and the 2-dimensional contour 312 of the epicardium, based on the Apical 2 Chamber image (2C) 310 along the long-axis direction. Moreover, the 2-dimensional contour detector 15 detects a 2-dimensional contour 321 of the endocardium and a 2-dimensional contour 322 of the epicardium, based on the MPR image 320 at the cross section along the line A. Further, the 2-dimensional contour detector 15 detects a 2-dimensional contour 331 of the endocardium and a 2-dimensional contour 332 of the epicardium, based on the MPR image 330 at the cross section along the line M. Furthermore, the 2-dimensional contour detector 15 detects a 2-dimensional contour 341 of the endocardium and a 2-dimensional contour 342 of the epicardium, based on the MPR image 340 at the cross section along the line B. The 2-dimensional contour detector 15 outputs coordinate information of the 2-dimensional contour of the endocardium and coordinate information of the 2-dimensional contour of the epicardium detected from the MPR images at each cross section, to the interpolation part 16.

Based on the coordinate information of the plurality of 2-dimensional contours detected by the 2-dimensional contour detector 15, the interpolation part 16 spatially interpolates the contour of the endocardium by using a spline function or the like, thereby obtaining the position of the 3-dimensional contour of the endocardium. Likewise, the interpolation part 16 spatially interpolates the contour of the epicardium by using a spline function or the like, thereby obtaining the position of the 3-dimensional contour of the epicardium. In the above example, the interpolation part 16 spatially interpolates the contour of the endocardium by using a spline function or the like based on the 2-dimensional contours of the endocardium detected from the Apical 4 Chamber image (4C) 300, the Apical 2 Chamber image (2C) 310, the MPR image 320, the MPR image 330 and the MPR image 340, thereby obtaining the position of the 3-dimensional contour of the endocardium. Likewise, the 3-dimensional contour of the epicardium is obtained. The coordinate information of the 3-dimensional contour of the endocardium and the coordinate information of the 3-dimensional contour of the epicardium obtained by the interpolation part 16 are outputted to the contour tracking part 12, and are set in the contour tracking part 12 as the initial contours of the endocardium and the epicardium.

The contour tracking part 12 performs pattern matching of the volume data acquired in each time phase by the ST method based on the initial contour of the endocardium obtained by the interpolation part 16, thereby obtaining the position of each of the points composing the 3-dimensional contour of the endocardium in each cardiac time phase. Likewise, the contour tracking part 12 obtains the position of each of the points composing the 3-dimensional contour of the epicardium in each cardiac time phase by the ST method. The contour tracking part 12 then tracks the 3-dimensional contour of the endocardium and the 3-dimensional contour of the epicardium.

As in the first embodiment, the computing part 20 obtains wall motion information such as strain and displacement in each cardiac time phase, based on coordinate information of each of the points composing the 3-dimensional contour of the endocardium and coordinate information of each of the points composing the 3-dimensional contour of the epicardium in each cardiac time phase. Then, the display controller 7 controls the display 81 to display the wall motion information in each cardiac time phase, for each cardiac time phase.

As described above, it becomes possible to obtain and display wall motion information in real time as in the aforementioned first embodiment, by detecting and tracking the 3-dimensional contour of the endocardium and the 3-dimensional contour of the epicardium in each cardiac time phase.

The display controller 7 may control the display 81 to display, for each cardiac time phase, the MPR image of each cardiac time phase. For example, as shown in FIG. 6A, the display controller 7 controls the display 81 to display, for each cardiac time phase, the Apical 4 Chamber image (4C) 300 and the Apical 2 Chamber image (2C) 310 of each cardiac time phase. Furthermore, as shown in FIG. 6B, the display controller 7 may control the display 81 to display, for each cardiac time phase, the MPR image 320, MPR image 330, and MPR image 340 at a cross section in the short-axis direction.

The contour tracking part 12 may track the contour of the endocardium and the contour of the epicardium, which have been set on each MPR image. In this case, the marker generator 13 generates a marker for indicating the contour of the endocardium and a marker for indicating the contour of the epicardium in each cardiac time phase. The display controller 7 controls the display 81 to display, for each cardiac time phase, the MPR image of each cardiac time phase. Furthermore, the display controller 7 may control the display 81 to sequentially display the marker indicating the contour of the endocardium and the marker indicating the contour of the epicardium in each cardiac time phase in the superimposed with the MPR image generated in each cardiac time phase.

For example, the contour tracking part 12 tracks the 2-dimensional contour of the endocardium and the 2-dimensional contour of the epicardium, which have been set on the MPR image 320 shown in FIG. 6B. In this case, the marker generator 13 generates a marker for indicating the 2-dimensional contour of the endocardium and a marker for indicating the 2-dimensional contour of the epicardium in each cardiac time phase. Then, the display controller 7 controls the display 81 to display, for each cardiac time phase, the MPR image 320 of each cardiac time phase, and further controls the display 81 to display the marker of the endocardium and the marker of the epicardium in each cardiac time phase in the superimposed state with the MPR image 320. Herein, the MPR image 320 was used as an example for the explanation, but it is also possible to display the MPR image on the other section and the marker in the superimposed state.

Moreover, as in the above first embodiment, the display controller 7 may assign a color corresponding to the size of the strain obtained in the computing part 20 to the region between the endocardium and the epicardium and control the display 81 to display in the superimposed state with the MPR image.

Furthermore, as in the first embodiment, the computing part 20 may obtain wall motion information such as strain, for each region recommended by the ASE. The computing part 20 may convert the peak values of the wall motion information of each region or the wall motion information to a graph and control the display 81 to display.

As in the first embodiment, the position of the 3-dimensional contour of the endocardium and the 3-dimensional contour of the epicardium, which are tracking objects, may be corrected at a predetermined timing in order to reduce the accumulation of tracking errors conducted over the course of a plurality of heartbeats using the ST method. For example, the correcting part 14 corrects the position of the 3-dimensional contour of the endocardium and the position of the 3-dimensional contour of the epicardium at every N number of heartbeats (N is an integer). Furthermore, the correcting part 14 may correct the position of the 3-dimensional contour of the endocardium and the position of the 3-dimensional contour of the epicardium at a timing at which an instruction for the correction is given by the operator. For example, every time a predetermined number of R waves are received by the controller 9, an instruction for the correction is given to the image processor 10A. Alternatively, when an instruction for the correction is given by the operator using an operating part 82, the instruction is outputted to the controller 9 and the controller 9 gives the instruction for the correction to the image processor 10A.

When the instruction for the correction is given by the controller 9, the 2-dimensional contour detector 15 executes the AQ method to detect the 2-dimensional contour of the endocardium and the 2-dimensional contour of the epicardium based on the MPR image data. For example, the 2-dimensional contour detector 15 detects the 2-dimensional contour of the endocardium and the 2-dimensional contour of the epicardium from the Apical 4 Chamber image (4C) 300. Furthermore, the 2-dimensional contour detector 15 detects the 2-dimensional contour of the endocardium and the 2-dimensional contour of the epicardium from the Apical 2 Chamber image (2C) 310. The interpolation part 16 obtains a position Paq of the 3-dimensional contour of the endocardium by using a spline function based on the 2-dimensional contours of the endocardium obtained from the two MPR images. At that moment, the contour tracking part 12 regards the position of the 3-dimensional contour of the endocardium obtained by the ST method as a position Pst. The correcting part 14 obtains a position P of an initial contour of the endocardium, which is to be newly set in the contour tracking part 12, in accordance with the above Formula 1. Then, the contour tracking part 12 tracks the initial contour of the endocardium obtained in accordance with the Formula 1. Likewise, the interpolation part 16 obtains a position Paq of the 3-dimensional contour of the epicardium based on the 2-dimensional contours of the epicardium, which have been obtained from the two MPR images. At that moment, the contour tracking part 12 regards the position of the 3-dimensional contour of the epicardium obtained by the ST method as a position Pst. The interpolation part 14 obtains the position of the initial contour of the epicardium in accordance with the above Formula 1, and the contour tracking part 12 tracks the initial contour of the epicardium.

Further, as in the modification of the first embodiment, the operator may designate the initial contour of the endocardium and the initial contour of the epicardium, and the interpolation part 15 may obtain by interpolating the contour of the endocardium and the contour of the epicardium in a 3-dimensional space based on the designated initial contours. For example, the display controller 7 controls the display 81 to display the Apical 4 Chamber image (4C) 300 and Apical 2 Chamber image (2C) 310 acquired in a preset cardiac time phase. For example, the display controller 7 controls the display 81 to display the Apical 4 Chamber image (4C) 300 and Apical 2 Chamber image (2C) 310 acquired in end diastole (a cardiac time phase in which an R wave has been detected). The display controller 7 controls the display 81 to display the Apical 4 Chamber image (4C) 300 and the Apical 2 Chamber image (2C) 310 while updating at time intervals of one heartbeat or more. The Apical 4 Chamber image (4C) 300 and the Apical 2 Chamber image (2C) 310 are images for setting an initial contour, and are equivalent to examples of the "tomographic image for initial contour setting" of the present invention.

The operator designates the 2-dimensional contour of the endocardium and the 2-dimensional contour of the epicardium on the Apical 4 Chamber image (4C) 300 and the Apical 2 Chamber image (2C) 310, by using the operation part 82. Coordinate information of the contour of the endocardium and coordinate information of the contour of the epicardium are outputted to the image processor 10A from the user interface 8. The interpolation part 16 obtains the initial contour of the endocardium in a 3-dimensional space by using a spline function or the like based on the coordinate information of the designated contour of the endocardium. Likewise, the interpolation part 16 obtains the initial contour of the epicardium in a 3-dimensional space based on the coordinate information of the designated contour of the epicardium. When the initial contour of the endocardium and the initial contour of the epicardium are thus designated, the contour tracking part 12 tracks, by the ST method, the 3-dimensional contour of the endocardium and the 3-dimensional contour of the epicardium. The computing part 20 obtains wall motion information such as strain and displacement in each cardiac time phase, based on the 3-dimensional contour in each cardiac time phase. The display controller 7 then controls the display 81 to display, for each cardiac time phase, the wall motion information in each cardiac time phase.

The display controller 7 may control the display 81 to display the MPR image 320 of each cardiac time phase, for each cardiac time phase, and further control the display 81 to display an MPR image for initial contour setting side by side with the MPR image 320. At this moment, the display controller 7 controls the display 81 to display the MPR image for initial contour setting while updating at time intervals of one heartbeat or more. The display controller 7 may control the display 81 to display the MPR image for initial contour setting at all times. Alternatively, the display controller 7 may control the display 81 to display the MPR image for initial contour setting only when setting an initial contour. Herein, the MPR image 320 is used as an example for explanation, but it is also possible to control the display 81 to display MPR images at other cross sections side by side with the MPR image for initial contour setting.

The display controller 7 may control the display 81 to display the MPR image 320 of each cardiac time phase, for each cardiac time phase, and control the display 81 to display, at a predetermined timing, an MPR image for initial contour setting acquired in a preset cardiac time phase instead of the MPR image 320. The operator designates the contour of the endocardium and the contour of the epicardium on the MPR image for initial contour setting displayed in the display 81, by using the operation part 82. When the initial contour is designated by the operator, the display controller 7 controls the display 81 to display, for each cardiac time phase, the MPR image 320 of the each cardiac time phase instead of the MPR image for initial contour setting.

In a case where the operator designates the initial contour of the endocardium and the initial contour of the epicardium, the contour detector 11A may be configured without the 2-dimensional contour detector 15.

As in the first embodiment, the ultrasonic image processing apparatus may be provided outside the ultrasonic imaging apparatus. This ultrasonic image processing apparatus comprises the aforementioned storage 6, display controller 7, user interface 8, image processor 10A and computing part 20. The ultrasonic image processing apparatus acquires a plurality of volume data whose acquisition times are sequential, from the external ultrasonic imaging apparatus, and obtains wall motion information by tracking the 3-dimensional contour of the endocardium and the 3-dimensional contour of the epicardium based on the plurality of volume data.

The image processor 10A includes a CPU and a storage (not illustrated) such as a CPU, a ROM, a RAM and an HDD. The storage stores image-processing programs for executing functions of the respective parts of the image processor 10A. The image-processing programs include a contour-detecting program for executing the function of the 2-dimensional contour detector 15, an interpolation program for executing the function of the interpolation part 16, a contour-tracking program for executing the function of the contour tracking part 12, a marker-generating program for executing the function of the marker generator 13, and a correction program for executing the function of the correcting part 14.

What is claimed is:

1. An ultrasonic image processing apparatus comprising:
a contour detector configured to receive ultrasonic image data acquired for each time phase by scanning a subject with ultrasonic waves, and detect a contour of a specific tissue based on the ultrasonic image data acquired in a predetermined time phase;
a contour tracking part configured to obtain a position of each of points composing the detected contour in the ultrasonic image data acquired for the each time phase, by pattern matching for the each time phase;
a computing part configured to obtain motion information indicating a motion state of the specific tissue in the each time phase, based on the position of each of the points composing the contour in the each time phase;
a display controller configured to control a display to display an ultrasonic image based on the ultrasonic image data acquired in the each time phase, for the each time phase, and moreover control the display to display the motion information in the each time phase obtained by the computing part, on each occasion of the each time phase;
a setting part configured to set a timing of correction and to periodically output the set timing; and
a correcting part configured to obtain a new contour of a tissue to become a tracking object for the contour tracking part, in response to the periodical timing output by the setting part,
wherein the contour tracking part obtains a position of each of points composing the new contour of the tissue in the each time phase, by pattern matching for the each time phase.

2. The ultrasonic image processing apparatus according to claim 1, wherein:
the contour detector receives tomographic image data acquired for the each time phase by scanning the subject with ultrasonic waves, as the ultrasonic image data, and detects a 2-dimensional contour of the specific tissue based on the tomographic image data acquired in the predetermined time phase;
the contour tracking part obtains a position of each of points composing the detected 2-dimensional contour in the tomographic image data acquired for the each time phase, by pattern matching for the each time phase;
the computing part obtains the motion information indicating the motion state of the specific tissue in the each time phase, based on the position of each of the points composing the 2-dimensional contour in the each time phase; and
the display controller controls the display to display a tomographic image based on the tomographic image data acquired in the each time phase, for the each time phase, and moreover controls the display to display the motion information in the each time phase obtained by the computing part, on each occasion of the each time phase.

3. The ultrasonic image processing apparatus according to claim 1, wherein:
the contour detector receives volume data acquired for the each time phase by scanning the subject with ultrasonic waves, as the ultrasonic image data, and detects a 3-dimensional contour of the specific tissue based on the volume data acquired in the predetermined time phase;
the contour tracking part obtains a position of each of points composing the detected 3-dimensional contour in the volume data acquired for the each time phase, by pattern matching for the each time phase;

the computing part obtains the motion information indicating the motion state of the specific tissue in the each time phase, based on the position of each of the points composing the 3-dimensional contour in the each time phase; and the display controller controls the display to display an ultrasonic image based on the volume data acquired in the each time phase, for the each time phase, and moreover controls the display to display the motion information in the each time phase obtained by the computing part, on each occasion of the each time phase.

4. The ultrasonic image processing apparatus according to claim 3, further comprising:

an image generator configured to obtain tomographic image data at a plurality of different cross sections, for each of the cross sections, based on the volume data acquired in the predetermined time phase, wherein:

the contour detector includes:

a 2-dimensional contour detector configured to detect a 2-dimensional contour of the specific tissue at each of the cross sections based on each of the plurality of tomographic image data; and an interpolation part configured to obtain a 3-dimensional contour of the tissue, by interpolating between positions of the 2-dimensional contours at the respective cross sections; and the contour tracking part obtains the position of each of the points composing the 3-dimensional contour obtained by the interpolation in the volume data acquired in the each time phase, by pattern matching for the each time phase.

5. The ultrasonic image processing apparatus according to claim 1, wherein:

the contour detector detects the contour of the tissue at the any timing; and the correcting part obtains the new contour of the tissue by weighting and adding the position of each of the points composing the contour of the tissue detected by the contour detector at the any timing and the position of each of the points composing the contour of the tissue obtained by the contour tracking part at the any timing.

6. The ultrasonic image processing apparatus according to claim 5, wherein:

the correcting part receives heartbeat information of the subject, and obtains the new contour of the tissue at time intervals of one heartbeat or more.

7. The ultrasonic image processing apparatus according to claim 5, further comprising:

an input part configured to give an instruction to obtain the position of the new contour, wherein when an operator gives the instruction by using the input part, the correcting part receives the instruction from the input part and obtains the new contour of the tissue at a timing of reception of the instruction.

8. The ultrasonic image processing apparatus according to claim 1, wherein:

the contour detector detects the contour of the specific tissue based on luminance information of the ultrasonic image data.

9. The ultrasonic image processing apparatus according to claim 8, wherein:

the contour detector detects the contour of the specific tissue based on the luminance information and preset shape information of the specific tissue.

10. An ultrasonic image processing apparatus comprising:

a contour tracking part configured to receive ultrasonic image data acquired for each time phase by scanning a subject with ultrasonic waves, and moreover receive designation of a contour of a specific tissue on an ultrasonic image based on the ultrasonic image data acquired in a predetermined time phase, thereby obtaining a position of each of points composing the designated contour in the ultrasonic image data acquired for the each time phase, by pattern matching for the each time phase;

a computing part configured to obtain motion information indicating a motion state of the specific tissue in the each time phase, based on the position of each of the points composing the contour in the each time phase;

a display controller configured to control a display to display an ultrasonic image based on the ultrasonic image data acquired in the each time phase, for the each time phase, and moreover control the display to display the motion information in the each time phase obtained by the computing part, on each occasion of the each time phase;

a setting part configured to set a timing of correction and to periodically output the set timing; and a correcting part configured to obtain a new contour of a tissue to become a tracking object for the contour tracking part, in response to the periodical timing output by the setting part, wherein the contour tracking part obtains a position of each of points composing the new contour of the tissue in the each time phase, by pattern matching for the each time phase.

11. The ultrasonic image processing apparatus according to claim 10, wherein:

the contour tracking part receives tomographic image data acquired for each time phase by scanning the subject with ultrasonic waves, as the ultrasonic image data, and moreover receives designation of a 2-dimensional contour of the specific tissue on a tomographic image based on the tomographic image data acquired in the predetermined time phase, thereby obtaining a position of each of points composing the designated 2-dimensional contour in the tomographic image data acquired in the each time phase, by pattern matching for the each time phase;

the computing part obtains the motion information indicating the motion state of the specific tissue in the each time phase, based on the position of each of the points composing the 2-dimensional contour in the each time phase; and the display controller controls the display to display a tomographic image based on the tomographic image data acquired in the each time phase, for the each time phase, and moreover controls the display to display the motion information in the each time phase obtained by the computing part, on each occasion of the each time phase.

12. The ultrasonic image processing apparatus according to claim 11, wherein:

the display controller receives heartbeat information of the subject, and controls the display to display a tomographic image for initial contour setting, based on the tomographic image data acquired in the predetermined time phase while updating at time intervals of one heartbeat or more; and when the 2-dimensional contour of the specific tissue is designated on the tomographic image for initial contour setting, the contour tracking part receives the designation and obtains the position of each of the points composing the designated 2-dimensional contour in the tomographic image data acquired in the each time phase, by pattern matching for the each time phase.

13. The ultrasonic image processing apparatus according to claim 10, further comprising:
- an image generator configured to receive volume data acquired for each time phase by scanning the subject with ultrasonic waves, as the ultrasonic image data, and obtain tomographic image data at a plurality of different cross sections, for each of the cross sections, based on the volume data acquired in the predetermined time phase; and
- an interpolation part configured to receive the designation of the 2-dimensional contour of the specific tissue in each of tomographic images based on the plurality of tomographic image data in the predetermined time phase, and interpolate between positions of 2-dimensional contours at the respective cross sections, thereby obtaining a 3-dimensional contour of the tissue, wherein:
- the contour tracking part obtains the position of each of the points composing the 3-dimensional contour obtained by the interpolation in the volume data acquired in the each time phase, by pattern matching for the each time phase;
- the computing part obtains the motion information indicating the motion state of the specific tissue in the each time phase, based on the position of each of the points composing the 3-dimensional contour in the each time phase; and
- the display controller controls the display to display an ultrasonic image based on the volume data acquired in the each time phase, and moreover controls the display to display the motion information in the each time phase obtained by the computing part, on each occasion of the each time phase.

14. The ultrasonic image processing apparatus according to claim 13, wherein:
- the display controller receives heartbeat information of the subject, and controls the display to display tomographic images for initial contour setting at the plurality of different cross sections acquired in the predetermined time phase while updating at time intervals of one heartbeat or more, respectively; and
- when the 2-dimensional contour of the specific tissue is designated on the updated plurality of tomographic images for initial contour setting, the interpolation part receives the designation and interpolates between the positions of the 2-dimensional contours at the respective cross sections, thereby obtaining the 3-dimensional contour of the tissue.

15. The ultrasonic image processing apparatus according to claim 12, wherein:
- the display controller controls the display to display the tomographic image based on the tomographic image data acquired in the each time phase, for the each time phase, and moreover controls the display to display the tomographic image for initial contour setting based on the tomographic image data acquired in the predetermined time phase while updating at the time intervals of one heartbeat or more, side by side with the tomographic image.

16. The ultrasonic image processing apparatus according to claim 12, wherein:
- the display controller controls the display to display the tomographic image based on the tomographic image data acquired in the each time phase, and controls the display to display the tomographic image for initial contour setting based on the tomographic image data acquired in the predetermined time phase while updating at the time intervals of one heartbeat or more, instead of the tomographic image, at a predetermined timing.

17. A method for processing an ultrasonic image, comprising:
- receiving ultrasonic image data acquired for each time phase by scanning a subject with ultrasonic waves, and detecting a contour of a specific tissue based on the ultrasonic image data acquired in a predetermined time phase;
- obtaining a position of each of points composing the detected contour in the ultrasonic image data acquired in the each time phase, by pattern matching for the each time phase;
- obtaining motion information indicating a motion state of the specific tissue in the each time phase, based on the position of each of the points composing the contour in the each time phase;
- displaying an ultrasonic image based on the ultrasonic image data acquired in the each time phase, and moreover displaying the motion information in the each time phase on each occasion of the each time phase;
- setting a timing of correction and to periodically output the set timing; and
- correcting to obtain a new contour of a tissue to become a tracking object for the contour tracking part, in response to the periodical timing output by the setting,
- wherein the contour tracking part obtains a position of each of points composing the new contour of the tissue in the each time phase, by pattern matching for the each time phase.

18. The method for processing an ultrasonic image according to claim 17, wherein:
- tomographic image data acquired for each time phase by scanning the subject with ultrasonic waves is received as the ultrasonic image data, and a 2-dimensional contour of the specific tissue is detected based on the tomographic image data acquired in the predetermined time phase;
- a position of each of points composing the detected 2-dimensional contour in the tomographic image data acquired in the each time phase is obtained by pattern matching for the each time phase;
- the motion information indicating the motion state of the specific tissue in the each time phase is obtained based on the position of each of the points composing the 2-dimensional contour in the each time phase; and
- a tomographic image based on the tomographic image data acquired in the each time phase is displayed for the each time phase, and moreover the motion information in the each time phase is displayed on each occasion of the each time phase.

19. The method for processing an ultrasonic image according to claim 17, wherein:
- volume data acquired for each time phase by scanning the subject with ultrasonic waves is received as the ultrasonic image data, and a 3-dimensional contour of the specific tissue is detected based on the volume data acquired in the predetermined time phase;
- a position of each of points composing the detected 3-dimensional contour in the volume data acquired for the each time phase is obtained by pattern matching for the each time phase;
- the motion information indicating the motion state of the specific tissue in the each time phase is obtained based on the position of each of the points composing the 3-dimensional contour in the each time phase; and an ultrasonic image based on the volume data acquired in the each time phase is displayed for the each time phase, and moreover the motion information in the each time phase is displayed on each occasion of the each time phase.

20. The method for processing an ultrasonic image according to claim 17, wherein:

a contour of the tissue is detected at any timing;

a position of each of the points composing the contour of the tissue detected at the any timing and the position of each of the points composing the contour of the tissue obtained by the pattern matching at the any timing are weighted and added, whereby a new contour of the tissue is obtained; and a position of each of points composing the new contour of the tissue in the each time phase is obtained by pattern matching for the each time phase.

21. A method for processing an ultrasonic image, comprising:

receiving ultrasonic image data acquired for each time phase by scanning a subject with ultrasonic waves, and moreover receiving designation of a contour of a specific tissue in an ultrasonic image based on the ultrasonic image data acquired in a predetermined time phase, thereby obtaining a position of each of points composing the designated contour in the ultrasonic image data acquired in the each time phase, by pattern matching for the each time phase;

obtaining motion information indicating a motion state of the specific tissue in the each time phase, based on the position of each of the points composing the contour of the each time phase;

displaying an ultrasonic image based on the ultrasonic image data acquired in the each time phase, for the each time phase, and moreover displaying the motion information in the each time phase, on each occasion of the each time phase;

setting a timing of correction and to periodically output the set timing; and correcting to obtain a new contour of a tissue to become a tracking object for the contour tracking part, in response to the periodical timing output by the setting, wherein the contour tracking part obtains a position of each of points composing the new contour of the tissue in the each time phase, by pattern matching for the each time phase.

22. The method for processing an ultrasonic image according to claim 21, wherein:

tomographic image data acquired for the each time phase by scanning the subject with ultrasonic waves is received as the ultrasonic image data, and moreover designation of a 2-dimensional contour of the specific tissue in a tomographic image based on the tomographic image data acquired in the predetermined time phase is received, whereby a position of each of points composing the designated 2-dimensional contour in the tomographic image data acquired in the each time phase is obtained by pattern matching for the each time phase; and the motion information indicating the motion state of the specific tissue in the each time phase is obtained based on the position of each of the points composing the 2-dimensional contour of the each time phase.

23. The method for processing an ultrasonic image according to claim 21, wherein:

volume data acquired for each time phase by scanning the subject with ultrasonic waves is received as the ultrasonic image data, and tomographic image data at a plurality of different cross sections are obtained for each of the cross sections, based on the volume data acquired in the predetermined time phase;

designation of a 2-dimensional contour of the specific tissue in each of tomographic images based on the plurality of tomographic image data in the predetermined time phase is received, and interpolation between positions of the 2-dimensional contours of the respective cross sections is performed, whereby a 3-dimensional contour of the tissue is obtained;

a position of each of points composing the 3-dimensional contour obtained by the interpolation in the volume data acquired in the each time phase is obtained by pattern matching for the each time phase; and the motion information indicating the motion state of the specific tissue in the each time phase is obtained based on the position of each of the points composing the 3-dimensional contour of the each time phase.

24. The method for processing an ultrasonic image according to claim 22, wherein:

heartbeat information of the subject is received, and a tomographic image for initial contour setting based on the tomographic image data acquired in the predetermined time phase is displayed while being updated at time intervals of one heartbeat or more; and when the 2-dimensional contour of the specific tissue is designated on the tomographic image for initial contour setting, the designation is received, and the position of each of the points composing the designated 2-dimensional contour in the tomographic image data acquired in the each time phase is obtained by pattern matching for the each time phase.

\* \* \* \* \*